US006432633B1

(12) United States Patent
Yamamoto et al.

(10) Patent No.: US 6,432,633 B1
(45) Date of Patent: Aug. 13, 2002

(54) IMMUNOASSAY METHOD OF HIV-1P24 ANTIGEN AND REAGENT THEREFOR

(75) Inventors: Katsuhiko Yamamoto; Akemi Yoshiki; Toshio Matsui; Atsushi Umetani, all of Tokyo (JP)

(73) Assignee: Fujirebio Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/621,625

(22) Filed: Jul. 21, 2000

(30) Foreign Application Priority Data

Jul. 28, 1999 (JP) .......................................... 11-213224

(51) Int. Cl.[7] .......................... C12Q 1/70; G01N 33/53; A61K 39/395; A61K 39/21
(52) U.S. Cl. ........................ 435/5; 435/7.1; 435/7.93; 435/7.94; 424/130.1; 424/160.1; 424/208.1
(58) Field of Search ........................ 435/7.1, 7.2, 7.21, 435/7.93, 7.94, 5; 530/300, 350; 424/130.1, 160.1, 208.1

(56) References Cited

U.S. PATENT DOCUMENTS 6,107,049 A * 8/2000 Allard et al. ................. 435/7.1

FOREIGN PATENT DOCUMENTS

SE   WO 91/13360 A1 * 9/1991

OTHER PUBLICATIONS

Schupbach et al., AIDS, vol. 10 (1996) pp. 1085–1090.
Jackson et al., J. of A.I.D.S., vol. 2 (1989) pp. 394–497.
Willoughby et al., Diagn. Microbiol. Infect. Ds., vol. 12 (1989) pp. 319–326.

* cited by examiner

Primary Examiner—Hankyel T. Park
Assistant Examiner—Stacy S. Brown
(74) Attorney, Agent, or Firm—Birch, Stewart, Kolasch & Birch, LLP

(57) ABSTRACT

An immunoassay method of the HIV-1p24 antigen by sandwich method, using at least one polyclonal antibody recognizing the HIV-1p24 antigen and at least two monoclonal antibodies recognizing the HIV-1p24 antigen, is provided together with a reagent therefor, to establish more highly sensitive assay of the HIV-1p24 antigen than conventionally.

2 Claims, 10 Drawing Sheets

T7<sup>p</sup>    : T7 promoter
lac<sup>o</sup>   : lac operator
SD         : Shine-Dalgarno sequence
TT         : T7 transcriptional terminator
Amp r      : β lactamase
lac I<sup>q</sup> : lac repressor
pBR322 ori : Replication origin Details of expression vector pw6A

| T7$^p$ | : T7 promoter |
| --- | --- |
| lac$^o$ | : lac operator |
| SD | : Shine-Dalgarno sequence |
| TT | : T7 transcriptional terminator |
| Amp r | : β lactamase |
| lac I$^q$ | : lac repressor |
| pBR322 ori | : Replication origin |

Fig. 1 Details of expression vector pw6A

IMMUNOASSAY METHOD OF HIV-1P24 ANTIGEN AND REAGENT THEREFOR

BACKGROUND OF THE INVENTION

1. Field of the Invention

The present invention relates to a sandwich immunoassay method of the HIV-1p24 antigen and a reagent for use in the sandwich immunoassay method.

2. Description of the Related Art

Acquired immunodeficiency syndrome (AIDS) means a group of diseases triggered by human immunodeficiency virus (HIV). Since HIV infection via blood was revealed, transfusion blood samples have been subjected to HIV antibody screening at blood centers all over Japan. Because the antibody titer never increases 6 to 8 weeks after HIV infection, however, the current HIV antibody screening methods are problematic in that the window-period (blank period) is present, in which blood infected with HIV cannot be detected although the blood is HIV positive.

Besides HIV antibody screening, alternatively, attempts have been made about the shortening of the window-period by screening blood for the presence of HIV antigen. HIV antigen is appropriately assayed by immunoassay methods for screening a great number of samples, but the antigenicity of HIV antigen is readily exposed to mutagenesis. Therefore, attempts have been made to assay the HIV-1p24 antigen with relatively stable antigenicity, in particular. HIV Antigen·EIA "ABBOTT" is commercially available as a product for HIV-1p24 antigen assay. So as to avoid the error in the detection of infected blood as much as possible, an assay method rapidly assaying a great number of samples at a higher detection sensitivity is desired.

It is a purpose of the invention to provide an immunoassay method of HIV-1p24 antigen at a high detection sensitivity and a reagent therefor.

SUMMARY OF THE INVENTION

So as to overcome such conventional problems, the present inventors have made investigations about the assay of HIV-1p24 antigen. The inventors have successfully assayed the HIV-1p24 antigen by a sandwich immunoassay method using a polyclonal antibody recognizing the C-terminal region of the HIV-1p24 antigen and two monoclonal antibodies recognizing the epitopes except the C-terminal region of the HIV-1p24 antigen, at a far higher detection sensitivity than those by the existing assay methods of the HIV-1p24 antigen. Thus, the invention has been achieved.

More specifically, the invention provides a sandwich immunoassay method of HIV-1p24 antigen, using a polyclonal antibody recognizing the C-terminal region of the HIV-1p24 antigen and at least two monoclonal antibodies recognizing the HIV-1p24 antigen and further, the HIV-1p24 antigen and the HIV-2p25 antigen, along with a reagent kit for use in the immunoassay method.

By using the inventive immunoassay method, HIV-1p24 antigen and HIV-2p25 antigen can be assayed at high detection sensitivity. Thus, the inventive immunoassay method can be widely used for the immunoassay of the HIV-1p24 antigen and HIV-2p25 antigen and the screening of transfusion blood.

DETAILED DESCRIPTION OF THE INVENTION

Figure 1:
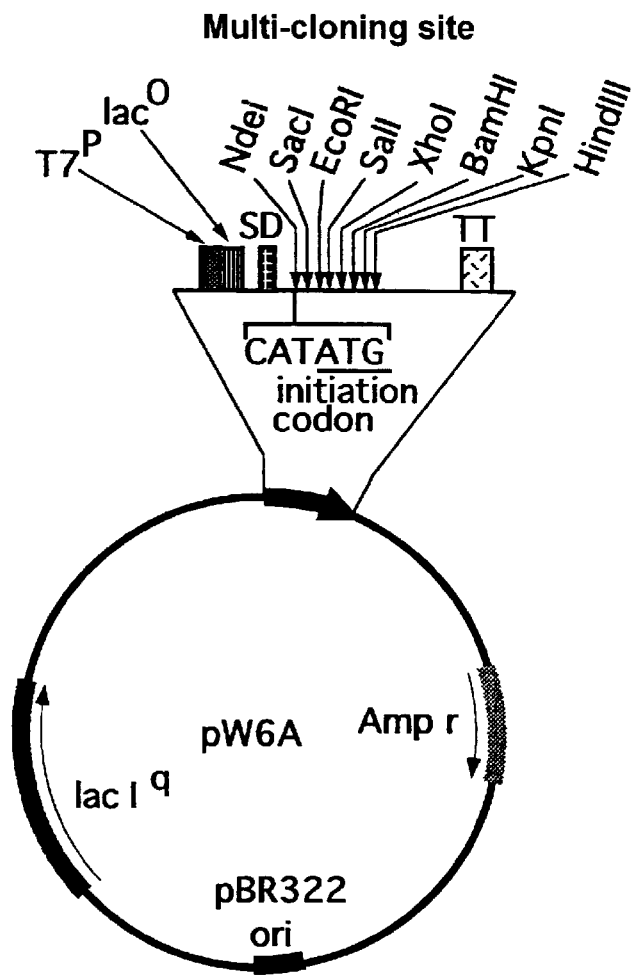
FIG. 1 is a restriction map of pW6A.

The invention will now be described in detail.

The amino acid sequence of HIV-1p24 antigen is described in Nature 313, p. 277–284 (1985). The amino acid sequence of the HIV-1p24 antigen corresponds to the amino acid sequence of the amino acids 133 to 363 in the HIV-1gag region. In the specification, hereinbelow, the amino acid 133 in the HIV-1gag region is expressed as the amino acid 1 of the HIV-1p24 antigen.

In accordance with the invention, the polyclonal antibody recognizing the HIV-1p24 antigen means that the principal recognition site of the polyclonal antibody corresponds to the HIV-1p24 antigen. Generally, the HIV-1p24 antigen is used as an immunogen for immunizing animals such as rabbit, guinea pig and goat; from the resulting anti-HIV-1p24 antiserum is purified the antibody fraction by a known method. The resulting antibody is used as the polyclonal antibody. As to the specificity of the polyclonal antibody, the HIV-1p24 antigen is to be recognized. Among them, the principal recognition site of the polyclonal antibody resides in the C-terminal region of the HIV-1p24. The term C-terminal region herein means a region in the amino acid sequence of the amino acids 1 to 231 of the HIV-1p24 antigen, the region being composed of an amino acid sequence of the amino acids around 200 up to 231 in the aforementioned amino acid sequence. The polyclonal antibody with the principal recognition site in the C-terminal region is an antibody recognizing the peptide p24bc of the amino acid sequence (the amino acid sequence of SEQ ID No:25) of the amino acids 113–303 in the amino acid sequence of the HIV-1p24 antigen, with no recognition of the peptide p24b of the amino acid sequence (the amino acid sequence of SEQ ID NO.23) of the amino acids 113–212 in the amino acid sequence of the HIV-1p24 antigen and the peptide p24c of the amino acid sequence (the amino acid sequence of SEQ ID NO:27) of the amino acids 213–303 in the amino acid sequence of the HIV-1p24 antigen.

More preferable is a polyclonal antibody recognizing as the principal recognition site a peptide of the amino acid sequence (the amino acid sequence of SEQ ID NO:13) of the amino acids 207–218 in the amino acid sequence of the HIV-1p24 antigen.

As the immunogen of the polyclonal antibody, use is made of any of purified natural antigens, recombinant antigens prepared by genetic engineering technology, and synthetic peptides. So as to efficiently recover the polyclonal antibody with the principal recognition site residing in the C-terminal region of the HIV-1p24 antigen, the peptide of the C-terminal region of the HIV-1p24 antigen can also be used as the immunogen. By our research works, however, simple use of purified natural antigens as the immunogen enabled the recovery of the polyclonal antibody with the principal recognition site residing in the C-terminal region of the HIV-1p24 antigen, advantageously.

In accordance with the invention, the number of polyclonal antibody means the number of reagent for use in the sandwich immunoassay. Among reagents comprising immobilized antibodies and labeled antibodies, more specifically, one reagent using polyclonal antibody is counted as one polyclonal antibody, while two reagents using polyclonal antibody are counted as two polyclonal antibodies. Generally, polyclonal antibodies are prepared from immunoglobulin purified from animal sera immunized with immunogens and then, plural polyclonal antibody lots are mixed together so as to avoid the individual difference in immunizing animals and the lot difference in antisera. Regarding the type of the inventive polyclonal antibody, the lot number of the mixed antisera or the purified polyclonal antibodies does not matter. Even when the polyclonal antibody samples with the same lot are used as variable antibodies such as immobilized antibody and labeled antibody for immunoassay, however, the number of the reagent is then the number of the inventive polyclonal antibody.

Because polyclonal antibodies are assemblies of plural antibodies, generally, polyclonal antibodies have plural recognition sites. Surprisingly, the inventive polyclonal antibody did not establish any sandwich immunoassay with a monoclonal antibody recognizing the C-terminal region of the HIV-1p24 antigen. More specifically, the inventive polyclonal antibody specifically recognizes the C-terminal region of the HIV-1p24 antigen despite the polyclonal characteristic properties. Thus, the polyclonal antibody had the principal recognition site residing in the C-terminal region.

In accordance with the invention, the monoclonal antibody recognizing the HIV-1p24 antigen means a monoclonal antibody establishing a sandwich immunoassay with a polyclonal antibody recognizing the HIV-1p24antigen. More specifically, the monoclonal antibody recognizes the HIV-1p24 antigen and has a recognition site different from that of the polyclonal antibody recognizing the HIV-1p24 antigen. In accordance with the invention, additionally, use is made of at least two monoclonal antibodies recognizing the HIV-1p24 antigen. Hence, the recognition sites of the monoclonal antibodies are essentially different from each other.

Preferably, the at least one polyclonal antibody recognizes the C-terminal region of the HIV-1p24 antigen, while one of the at least two monoclonal antibodies recognizes the N-terminus of the HIV-1p24 antigen and the remaining one thereof recognizes an intermediate site of the HIV-1p24 antigen.

The monoclonal antibody recognizing the N-terminus of the HIV-1p24 antigen means a monoclonal antibody recognizing the peptide p24a+ (amino acid sequence described as SEQ ID NO: 29) of the amino acid sequence of the amino acids 1 to 112 in the amino acid sequence of the HIV-1p24 antigen, while the monoclonal antibody never recognizes the peptide p24a of the amino acid sequence (the amino acid sequence described as SEQ ID NO: 19) of the amino acids 22 to 112 in the amino acid sequence of the HIV-1p24 antigen. A more preferable embodiment of the monoclonal antibody is a monoclonal antibody recognizing a peptide of the amino acid sequence (the amino acid sequence described as SEQ ID NO: 14) of the amino acids 1 to 27 in the amino acid sequence of the HIV-1p24 antigen.

Additionally, the monoclonal antibody recognizing the intermediate site of the HIV-1p24 antigen means a monoclonal antibody recognizing the peptide p24ab (the amino acid sequence described as SEQ ID NO:21) of the amino acid sequence of the amino acids 22 to 212 in the amino acid sequence of the HIV-1p24 antigen, while the monoclonal antibody never recognizes the peptide p24a of the amino acid sequence (the amino acid sequence described as SEQ ID NO:19) of the amino acids 22 to 112 in the amino acid sequence of the HIV-1p24 antigen and the peptide p24b of the amino acid sequence (the amino acid sequence described as SEQ ID NO:23) of the amino acids 113 to 212 in the amino acid sequence of the HIV-1p24 antigen. A more preferable embodiment of the monoclonal antibody is a monoclonal antibody recognizing the peptide of the amino acid sequence (the amino acid sequence described as SEQ ID NO:15) of the amino acids 107 to 118 in the amino acid sequence of the HIV-1p24 antigen.

As the immunogen for preparing the monoclonal antibody, use can be made of any of purified natural antigens, recombinant antigens prepared by genetic engineering technology, and synthetic peptides. So as to recover a monoclonal antibody recognizing the N-terminus of the HIV-1p24 antigen, the peptide of the N-terminus of the HIV-1p24 antigen is preferably used; and so as to recover a monoclonal antibody recognizing the intermediate site of the HIV-1p24, a peptide at the intermediate site of the HIV-1p24 is preferably used. However, a monoclonal antibody with a specificity depending on the purpose is satisfactorily selected, even when any type of immunogens is used. Therefore, the immunogen is not limited to these immunogens.

The monoclonal antibody can be prepared by known methods for example the method of Kohler and Milstein (Nature 256 495 1975) and the method of Shoeler (Nature 285 446 1980). In other words, immunizing animals such as mouse, rat and hamster are immunized with the immunogens to confirm the increase of the antibody titer; and then, the resulting antibody-generating cell and a tumor cell are fused together, to prepare a hybridoma. Then, the hybridoma is selected by using a selection culture medium; and the culture supernatant is assayed by an appropriate immunoassay method such as enzyme immunoassay, to select a clone generating the intended monoclonal antibody specific to HIV-1p24. The selected clone is cloned by methods such as the limited dilution method, to prepare a monoclonal antibody.

By analysis and purification means such as salting-out, ion exchange chromatography, and affinity chromatography immobilized with Protein A, the monoclonal antibody prepared by the aforementioned method is recovered from the ascites fluid of a pristan-treated mouse after the administration of the hybridoma generating the monoclonal antibody or the culture supernatant of the hybridoma generating the monoclonal antibody.

The monoclonal antibody described in the following examples was prepared by first preparing a hybridoma generating the monoclonal antibody by the known method using the purified HIV-1p24 antigen as the immunogen. A monoclonal antibody efficiently establishing a sandwich immunoassay with the polyclonal antibody recognizing the C-terminal region of the HIV-1p24 antigen was selected, to analyze the recognition site by using individual peptides of the HIV-1p24 antigen. Consequently, the monoclonal antibodies recognizing the N-terminus and intermediate site of the HIV-1p24 were preferable. Among them, the hybridomas generating the monoclonal antibodies recognizing the N-terminus and intermediate site of the HIV-1p24 were defined as p24N1-9 and p24N3-3, respectively, and were then deposited under Accession Nos. FERM P-17276 and FERM P-17275, respectively, at the Life Engineering and Industrial Technology Research Institute, the Agency of Industrial Science and Technology, at 1–3, Higashi 1-chome, Tsukuba-shi, Ibaraki-ken, Japan (Zip Code: 305-8566).

Because the HIV-1p24 antigen and HIV-2p25 antigen are highly homologous, the polyclonal antibody and monoclonal antibodies in accordance with the invention can be used as antibodies simultaneously recognizing the HIV-1p24 antigen and HIV-2p25 antigen. The polyclonal antibody prepared below in Example 7, the monoclonal antibody generated by the hybridoma p24N1-9 and the monoclonal antibody generated by the hybridoma p24N3-3 were all antibodies recognizing the HIV-1p24 antigen and HIV-2p25 antigen. Because the sandwich immunoassay using such antibodies can detect the HIV-1 antibody and HIV-2 antibody at one single assay, the sandwich immunoassay is very convenient for use in the screening of transfusion blood and the like for the presence of the HIV antibody.

The inventive immunoassay method is applicable for any of known immunoassay methods based on the assay principle of sandwich assay. So as to assay a great number of samples at a high sensitivity in a simple and rapid manner, an enzyme-labeled sandwich immunoassay using immobilizing method is preferable. More preferably, the polyclonal antibody having the principal recognition site at the C-terminus of HIV-1p24 is used as an enzyme-labeled antibody, while the two monoclonal antibodies recognizing the N-terminus and intermediate site of HIV-1p24 are used as the immobilized antibodies.

The enzyme labeling of the polyclonal antibody having the principal recognition site at the C-terminus of HIV-1p24 can satisfactorily be labeled directly by known covalent bonding and the like or can be indirectly labeled using other binding pairs such as biotin-avidin. The polyclonal antibody can be labeled by known methods, but preferably, the polyclonal antibody is satisfactorily labeled with a bifunctional cross-linking reagent as Fab' form of it. As the labeling enzyme, use is made of know enzymes such as alkali phosphatase (described hereinbelow as ALP in the specification), peroxidase and β-galactosidase. So as to provide an assay system at a high detection sensitivity, ALP with a preferable chemiluminescent substrate is preferably used.

So as to immobilize the monoclonal antibodies, known methods such as physical adsorption and chemical binding using crosslinking agents can appropriately be used. For immobilization, the two monoclonal antibodies are mixed together and immobilized, but the two monoclonal antibodies are individually immobilized on an immobilizing phase; and thereafter, the individual antibody-bound immobilizing phases are mixed together for use in the assay. For stably producing the assay reagent, immobilizing phases with the individual monoclonal antibodies immobilized thereon are preferably mixed together for use. As the immobilizing phase, use can appropriately be made of known immobilizing phases such as ELISA plates, polystyrene beads, and magnetic particles. For using a mixture of such immobilizing phases, preferably, particles such as magnetic particle are used.

Specific examples of the inventive immunoassay method includes a method comprising reaction of 100 µl of a sample with 250 µl of a magnetic particle bonded with the two monoclonal antibodies at 37° C. for 10 minutes, rinsing, addition of 250 µl of an ALP-labeled polyclonal antibody solution for reaction at 37° C. for another 10 minutes, rinsing, addition of 200 µl of a luminescent substrate and assaying of the luminescent level at 37° C. after 5 minutes. The assay method can preferably be carried out with a full-automatic chemiluminescent immunoassay apparatus, Lumipulse $f$ (manufactured by Fujirebio Inc.).

The inventive reagent means an assay reagent required for assaying the HIV-1p24 antigen and combinations thereof and includes reagents such as antibody-bound immobilizing phase, enzyme-labeled antibody, substrate, sample dilution solution, rinsing solution, positive control, and negative control. So as to rapidly assay a great number of samples in a simple manner, the inventive reagent is preferably composed in the form of a reagent possibly assayed with a full-automatic enzyme immunoassay apparatus.

Furthermore, the assaying sample is with no specific limitation. For example, various body fluids such as serum, plasma, whole blood, urine, and lymphatic fluid and cell or tissue extracts can be used for assaying the HIV-1p24 antigen.

The antigenicity of HIV frequently mutates. Therefore, assays with a combination of antibodies with two recognition sites, such as general sandwich immunoassay, are at high probabilities of no assay chance of the HIV-1p24 antigen when the antigen site of the antibody used is modified. For assaying such readily mutating antigen, polyclonal antibodies rather than monoclonal antibodies are preferably used. However, the preparation of plural polyclonal antibodies capable of progressing sandwich reaction at a high reproducibility is difficult in the sense of stable supply of immunoassay reagents.

Because the assay method of the inventive constitution comprises a combination of one polyclonal antibody and at least two monoclonal antibodies, namely a combination of antibodies with at least three recognition sites in the whole immunoassay system, on contrast, the method is hardly affected by the influence of the mutation of the antigenicity. Additionally, the monoclonal antibodies in combination with the polyclonal antibody enable the preparation of antibodies reacting with individual recognition sites at the N-terminus, intermediate region and C-terminus of the HIV-1p24 antigen at a high reproducibility; Because the recognition sites of at least the three antibodies differ from each other, antigen-antibody complexes can efficiently be formed for sandwich assay. Thus, the inventive method is at a higher detection sensitivity than the sensitivities of the conventional methods.

As shown in the following examples, the assay sensitivity of HIV Antigen·EIA "ABBOTT" for use as one of the existing HIV-1p24 antibody assay reagents is 12 µg/ml. The assay conditions of the product are as follows: the sample volume is 200 µl and the total assay period of time is 5.5 hours. On contrast, the detection sensitivity of the inventive immunoassay method was 4 pg/ml, by using the sample volume of 100 µl and the total assay period of 25 minutes.

The detection sensitivity of the immunoassay method is influenced by the sample volume and immunoreaction time for use. In terms of the sample volumes for use in the two assay methods, the inventive immunoassay method is at a sensitivity as high as 6-fold that of the existing method, while the assay period is 1/10-fold or less. Additionally, the existing full-automatic chemiluminescent immunoassay apparatus, Lumipulse ƒ (Fujirebio Inc.) can be used by the inventive assay method. Therefore, the inventive immunoassay method is shown to be a preferable assay method for screening of the HIV-1p24 antigen.

The invention is described in more detail in the following reference examples and examples.

EXAMPLE 1

Preparation of Recombinant DNA (1) Preparation of pW6A

Using the T7 promoter and T7 terminator gene of pGEMEX-1 (manufactured by Promega Co.), the ampicillin-resistant gene of pGEX-2T (manufactured by Pharmacia Co.), lac Iq repressor gene and ori to insert a site at which the lac repressor could be bound downstream the T7 promoter and a termination codon at the multi-cloning site, an expression vector pW6A was prepared. The restriction endonuclease map of the prepared pW6A is shown in FIG. 1.

(2) Preparation of pHIV24-2

As the DNA fragment encoding HIV-1gag protein, λWMJ-1 [Science, 232, p. 1548–1553 (1986)] cloned from a virus isolated from an HIV-infected person was used. λWMJ-1 was digested with a restriction endonuclease Bgl2 and blunt ended with Mung Bean nuclease, and was further digested with a restriction endonuclease NsiI; and the resulting digestion product was then isolated and purified by using agarose electrophores is, to recover a 845-bp DNA fragment carrying the gag gene.

Additionally, λWMJ-1 was digested with restriction endonucleases Pvu2 and NsiI and isolated and purified by using agarose electrophoresis, to recover a DNA fragment of 104 bp.

Plasmid pUC9 [Gene, 2, p.95–113 (1977)] digested with a restriction endonuclease PstI and dephosphorylated with ALP was simultaneously ligated to the two fragments, to prepare pHIV24-2. The objective DNA fragment inserted in pUC9 is shown as SEQ ID NO. 1. pHIV24-2 has a stop codon immediately after the objective DNA sequence inserted.

(3) Preparation of Plasmid for Analysis

So as to express the peptide for analysis, a plasmid was prepared. Firstly, a primer was prepared for preparing a DNA fragment to be inserted in the plasmid by PCR.

Using a DNA sequencer (manufactured by Perkin-Elmer Co.), an oligonucleotide was prepared. Primers 24F1, 24F2, 24F3, 24F+1, 24F+2, 24R1, 24R2, 24R3, 25F and 25R were prepared.

The primers 24F1, 24F2, 24F3, 24F+1, 24F+2, 24R1, 24R2, 24R3, 25F and 25R are individually shown as SEQ-ID NOS: 3-12, respectively.

The DNA fragment to be inserted in the plasmid for analysis (sometimes referred to as fragment in the specification) was prepared by PCR. Using pHIV24-2 prepared in the Example 1 (1), the following fragments encoding parts of HIV-1gag were prepared;

primers 24F1 and 24R3 were used to prepare the fragment 24abc; primers 24F1 and 24R1 were used to prepare the fragment 24a; primers 24F1 and 24R2 were used to prepare the fragment 24ab; primers 24F2 and 24R2 were used to prepare the fragment 24b; primers 24F2 and 24R3 were used to prepare the fragment 24bc; primers 24F3 and 24R3 were used to prepare the fragment 24c; and primers 24F+1, 24F+2 and 24R1 were used to prepare the fragment 24a+.

As the material encoding HIV-2gag, a fragment 25 was prepared by preparing, as a PCR template, DNA from the MOLT-4/GH-1 cell line infected with the HIV-2 GH-1 μline in a sustained manner and using the primers 25F and 25R.

pW6A digested with restriction endonucleases NdeI and BamHI and then dephosphorylated with ALP was ligated to the fragment 24abc digested with NdeI and BamHI, to prepare plasmid pHIV150 abc.

pW6A digested with restriction endonucleases NdeI and XhoI and dephosphorylated with ALP was ligated to the fragment 24a digested with NdeI and XhoI, to prepare plasmid pHIV150 a.

pW6A digested with restriction endonucleases NdeI and XhoI and dephosphorylated with ALP was ligated to the fragment 24ab digested with NdeI and XhoI, to prepare plasmid pHIV150 ab.

pW6A digested with restriction endonucleases EcoRI and XhoI and dephosphorylated with ALP was ligated to the fragment 24b digested with EcoRI and XhoI, to prepare plasmid pHIV150 b.

pW6A digested with restriction endonucleases EcoRI and BamHI and dephosphorylated with ALP was ligated to the fragment 24bc digested with EcoRI and BamHI, to prepare plasmid pHIV150 bc.

pW6A digested with restriction endonucleases EcoRI and XhoI and dephosphorylated with ALP was ligated to the fragment 24c digested with EcoRI and BamHI, to prepare plasmid pHIV150 c.

pW6A digested with restriction endonucleases EcoRI and BamHI and dephosphorylated with ALP was ligated to the fragment 24a+ digested with EcoRI and XhoI, to prepare plasmid pHIV151 a+.

pW6A digested with restriction endonucleases NdeI and XhoI and dephosphorylated with ALP was ligated to the fragment 25 digested with NdeI and XhoI, to prepare plasmid pHIV152.

EXAMPLE 2

Expression and Preparation of Peptide (1) Expression and Purification of p24-2

The plasmid pHIV24-2 prepared in Example 1 (1) was inserted in a host *Escherichia coli* BL21 (DE3) and cultured in an LB culture medium supplemented with 20 μg/ml ampicillin at 37° C. At OD 660 nm=0.5 to 0.7, 4 mM IPTG was added for induction, to culture the bacteria for 16 hours, for the expression. The culture was centrifuged to discard the supernatant, to recover the bacteria as pellet.

To the recovered *Escherichia coli* were added 1 mM EDTA, 100 mM sodium chloride, and 50 mM Tris-HCl buffer, pH 8.0, followed by addition of a protein decomposition inhibitor PMSF, for treatments with lysozyme and DNAase. Then, the resulting mixture was rinsed in 2 mM EDTA, 10 mM DTT, 2 M urea, and 50 mM Tris-HCl buffer, pH 8.0 and further rinsed in 10 mM DTT, 2 M urea, and 50 mM Tris-HCl buffer, pH 8.0. Subsequently, the objective expression product was extracted in 10 mM DTT, 4 M urea, and 10 mM Tris-sodium hydroxide buffer, pH 10.5.

Subsequently, the fraction was purified by chromatography on a phenyl Sepharose 6FF column. The purified product was rinsed in 1 mM DTT, 0.7 M ammonium sulfate, and 10 mM Tris-HCl buffer, pH 8.0. Furthermore, the product was rinsed in ammonium sulfate at a concentration modified to 0.6 M and was then eluted with 1 mM DTT, 0.4

M ammonium sulfate and 10 mM Tris-HCl buffer, pH 8.0. Then, the fraction was purified by chromatography on a hydroxyapatite column, followed by rinsing with 1 mM DTT, 0.1% SDS, 10 mM Tris-HCl buffer, pH 8.0 and additionally with 1 mM DTT, 0.1% SDS, 0.1 M sodium phosphate buffer, pH 7.0. Additionally, rinsing was repeated with 1 mM DTT and 0.1% SDS on a step-wise gradient of the sodium phosphate concentration with the increase from 0.2 M to 0.3 M. Then, elution with 1 mM DTT, 0.1% SDS and 0.5 M sodium phosphate buffer, pH 7.0 was effected. The fraction was purified by gel filtration with Sephadex G-25 and eluted with 0.1% SDS and 10 mM Tris-HCl buffer, pH 8.0. The recovered expression product was designated p24-2. The amino acid sequence of p24-2 is shown as SEQ ID NO:2.

(2) Expression and Preparation of peptide for Analysis

The individual plasmids for analysis as prepared in Example 1 (3) were introduced in a host *Escherichia coli* BL21 (DE3). The resulting host was then cultured in an LB culture medium supplemented with 20 μg/ml ampicillin at 37° C. for 16 hours. Furthermore, 20-fold dilution with the LB culture medium supplemented with 20 μg/ml ampicillin was effected for culturing at 37° C. for 2 hours, followed by addition of IPTG to a final concentration of 200 μg/ml and culturing for 3 hours for expression. *Escherichia coli* was centrifuged to discard the supernatant, and the resulting pellet was recovered. The recovered *Escherichia coli* was suspended in 100 μl of 100 mM sodium chloride, 50 mM Tris-HCl, pH 8.0 and 0.1 mM EDTA, followed by addition of 50 μl of a buffer containing 30% SDS, 15% 2-mercaptoethanol and 15% glycerin under agitation. Furthermore, 5-minute treatment in boiling water was effected, followed by ultrasonic treatment until the viscosity was lost, to prepare a sample for Western blotting.

The peptide purified from pHIV150abc was defined p24abc; the peptide purified from pHIV150a was defined p24a; the peptide purified from pHIV150ab was defined p24ab; the peptide purified from pHIV150b was defined p24b; the peptide purified from pHIV150bc was defined p24bc; the peptide purified from pHIV150c was defined p24c; the peptide purified from pHIV151a+ was defined p24a+; and the peptide purified from pHIV152 was defined p25.

The amino acid sequence and nucleotide sequence of p24abc are shown as SEQ ID NOS:17 and 16, respectively; the amino acid sequence and nucleotide sequence of p24a are shown as SEQ ID NOS:19 and 18, respectively; the amino acid sequence and nucleotide sequence of p24ab are shown as SEQ ID NOS:21 and 20, respectively; the amino acid sequence and nucleotide sequence of p24b are shown as SEQ ID NOS. 23 and 22, respectively; the amino acid sequence and nucleotide sequence of p24bc are shown as SEQ ID NOS:25 and 24, respectively; the amino acid sequence and nucleotide sequence of p24c are shown as SEQ ID NOS:27 and 26, respectively; the amino acid sequence and nucleotide sequence of p24a+ are shown as and SEQ ID NOS:29 and 29, respectively; and the amino acid sequence and nucleotide sequence of p25 are shown as SEQ ID NOS:31 and 30, respectively.

EXAMPLE 3

Purification of HIV-1p24 Antigen

HIV-1-infected cell (MOLT-4/HIV-1) was cultured in an RPMI 1640 culture medium containing 10% FCS (fetal calf serum). From the culture supernatant was purified the virus by the sucrose-density gradient centrifugation method. The purified virus was suspended in TNE buffer, pH 7.2, followed by addition of 0.1% SDS and 4 mM DTT for treatment at 100° C. for 5 minutes and centrifugation at 1,000 g for 10 minutes. The resulting supernatant was defined as an inactivated virus-solubilized solution. The inactivated virus-solubilized solution was adsorbed on a hydroxyapatite column, which was then rinsed in 0.1 M phosphate buffer, pH 7.0. The HIV-1p24 antigen was eluted with 0.25 M phosphate buffer and defined as purified p24 antigen.

EXAMPLE 4

Preparation of Monoclonal Antibody

As an adjuvant, the Freund's adjuvant was suspended in the p24-2 antigen solution purified in Example 2 (1), while β-glucan powder (Opti Vant; manufactured by Intergen Co.) was suspended in the purified p24 antigen solution prepared in Example 3. The resulting suspensions were individually peritoneally administered at 20 μl/0.5 ml per BALB/c mouse. At an interval of 10 days to 2 weeks, the suspensions were inoculated into these mice three times; blood was drawn from the caudal veins of the mice. The serum antibody titer was examined by ELISA using a 96-well assay plate immobilized with the immunogens.

The antigen prepared in Example 3 was additionally boosted twice until satisfactory antibody response was recovered. Three days after the final immunization, spleen was resected for cell fusion according to the routine Kohler & Milstein method (Nature 256, 495, 1975). As the parent cell, use was made of a mouse myeloma cell line P3-X 63-Ag8-U1 (P3U1); and as a fusing agent, use was made of polyethylene glycol. The fused cell was cultured in a HAT selection culture medium; about 10 days later, the culture supernatant was subjected to primary screening by ELISA. More specifically, the p24 antigen prepared in Example 2 or 3 was immobilized at a concentration of 1 μg/ml in a 96-well plate, followed by reaction with the culture supernatant for detection with anti-mouse Ig-POD (manufactured by Daco, Co.). The cells selected in such manner in the wells were cloned by the limited dilution method, to establish hybridomas. The hybridomas p24N1-9, p24N3-3, p24N1-2 and p24-21 were hybridomas generating antibodies specifically reacting with HIV-1p24. Among them, the hybridomas p24N1-9 and p24N3-3 were deposited at the Life Engineering and Industrial Technology Research Institute, supra. Their accession Nos. were FERM P-17276 and FERM P-17275, respectively.

The individual hybridomas were inoculated peritoneally at about 1×10$^7$ cells per mouse in mice preliminarily peritoneally administered with pristan of 0.5 ml. One week to 10 days later, the retained ascites fluid was collected. By using protein A column (manufactured by BioRad, Co.) and the MAPS-II kit buffer, monoclonal antibodies were purified. The monoclonal antibodies generated by the hybridomas p24N1-9, p24N3-3, p24N1-2 and p24-21 were defined as monoclonal antibodies p24N1-9, p24N3-3, p24N1-2 and p24-21, respectively.

The individual monoclonal antibodies were subjected to isotyping by the Western blotting using a kit manufactured by Amersham, Co. Consequently, all the antibodies were IgG1, κ.

EXAMPLE 5

Test of Reactivity of Monoclonal Antibodies

The reaction specificities of the monoclonal antibodies prepared in Example 4 were examined by Western blotting method. More specifically, the recombinant antigens p24a+, p24a, p24b, p24c, p24ab, p24bc, p24-2 and p25 (HIV-2gag) prepared in Example 2 and the purified p24 antigen prepared in Example 3 were dissolved in a buffer containing 10% SDS, 5% 2-mercaptoethanol and 5% glycerin; and the resulting mixtures were electrophoresed on 15% polyacrylamide gel and transferred on nitro cellulose membranes. The transfer membranes were left to stand in PBS containing 1% skim milk at 4° C. overnight, for masking. The transfer membranes were immersed in a solution containing the monoclonal antibodies prepared in Example 4 for one-hour reaction; and thereafter, the resulting reaction products were rinsed in PBS containing 0.05% Tween 20 and detected by Bectastein ABC elute kit (Bectar Co.), to compare their reactivity. The results are shown in Table 1.

TABLE 1

Epitope analysis of anti-HIV-lp24 monoclonal antibodies

| Antigen | Monoclonal antibodies | | | |
|---|---|---|---|---|
| | p24N1-9 | p24N3-3 | p24N1-2 | p24-21 |
| p24a+ | + | − | − | − |
| p24a | − | − | − | − |
| p24ab | − | + | + | − |
| p24b | − | − | + | − |
| p24bc | − | − | + | + |
| p24c | − | − | − | − |
| p24abc | − | + | + | + |
| p-natural p24 | + | + | + | + |
| p25 | + | + | + | + |

It is shown that the p24N1-9 antibody recognizes the N-terminus of the p24 antigen; the p24N3-3 antibody recognizes an intermediate site of the p24 antigen; the p24N1-2 antibody recognizes a site toward the C-terminus of the p24 antigen from the intermediate site thereof; and the p24-21 antibody recognizes the C-terminal region of the p24 antigen.

EXAMPLE 6

Epitope Classification at Combination Tests of Monoclonal Antibodies

Four antibodies, namely the p24-21 antibody prepared in Example 4, and the anti-HIV-1p24 monoclonal antibodies prepared by the same method as described in Example 4, ie. YAM24-12 antibody, YAM24-7 antibody and YAM24-9 antibody were individually prepared into antibody-sensitized particles and ALP-labeled antibodies, to examine their reactivities at combination tests.

(1) Preparation of Antibody-bound Particle 0.15 ml of 50 mg/ml ferrite particle (manufactured by Nippon Paint Co.) was placed, to which was added 280 μl of 720 μg/ml YAM24-12 antibody solution, followed by agitation and subsequent agitation at 25° C. in an end-over-end fashion for one hour. The ferrite particle was collected magnetically with a magnet to discard the supernatant; then, the resulting particle was rinsed twice in 0.4% NaCl solution, followed by addition of 2 ml of 50 mM Tris-HCl buffer, pH 7.2 containing 2% BSA, agitation and subsequent agitation overnight at 37° C. in an end-over-end fashion. The resulting solution was diluted 25-fold for use in reaction. The YAM24-7 antibody, the YAM24-9 antibody and the p24-21 antibody were also prepared as such antibody-bound particles.

(2) Preparation of ALP-labeled Antibodies 1.2 ml of 720 μg/ml YAM24-12 antibody solution was placed, which was then added to a column G-25 (manufactured by Pharmacia, Co.) equilibrated with 0.1 M citrate buffer, pH 3.5, for substitution with the buffer. To the resulting solution was added 43.6 μl of 94 μg/ml pepsin solution, and the resulting solution was left to stand at 37° C. for one hour and was then modified to pH around neutrality by using Tris-HCl buffer, which was then added to a column Superdex 200 (manufactured by Pharmacia Co.) for purification by gel filtration. The single peak of the resulting fraction at the absorbance at 280 nm was pooled, which was defined as YAM24-12 antibody F(ab')$_2$ fragment. To 1.53 ml of the F(ab')$_2$ fragment solution was added 76.5 μl of 0.2 M 2-mercaptoethylamine (referred to as 2-MEA hereinafter), and the resulting mixture was left to stand at 37° C. for 4 hours for reduction treatment. The resulting solution was added to the G-25 column to discard 2-MEA and recover YAM24-12 antibody Fab' fragment. 1 ml of 10 mg/ml ALP solution at a high specific activity was added to G-25 equilibrated with 0.1 M phosphate buffer, pH 6.3, for substitution with the buffer. To the resulting solution was added 51.6 μl of a dimethylformamide solution of 10 mg/ml N-(4-maleimidebutyryloxy)-succinimide (referred to as GMBS hereinafter), and the resulting mixture was left to stand at 37° C. for one hour. The solution was added to a G-25 column equilibrated with 0.1 M phosphate buffer, pH 7.0, to discard excess GMBS to prepare maleimidated ALP. The previously prepared YAM24-12 antibody Fab' fragment solution of 2.5 ml and the maleimidated ALP solution of 203.5 μl were mixed together and left to stand overnight at room temperature, to prepare ALP-labeled antibody, to which was then added 5.4 μl of 0.5 M 2-MEA solution. The resulting solution was left to stand at 37° C. for one hour, to block excess maleimide group. The resulting solution was added to Superdex 200 column, for purification. Among some peaks at the absorbance at 280 nm, a peak of a molecular weight at a ratio of Fab': ALP being 1:1 was pooled and defined as purified ALP-labeled antibody. ALP-labeled antibodies of the YAM24-7 antibody, YAM24-9 antibody and p24-21 antibody were also prepared in the same manner.

(3) Assay of p24 Antigen Using Antibody-bound Particle and ALP-labeled Antibody

The antibody-bound particle prepared in Example 6 (1) was adjusted to 0.15 mg/ml; to 0.25 ml thereof was added 50 μl each of the inactivated cultured HIV antigen solution at p24 antigen concentrations of 0, 12.5, 25, 50 and 100 pg/ml, for reaction at 37° C. for 10 minutes. After rinsing with a magnet, 0.25 ml of a solution of the ALP-labeled antibody prepared in Example 6 (2) after dilution to 0.5 μg/ml, was added to the resulting rinsed solution, for another reaction at 37° C. for 10 minutes. After rinsing with a magnet, 200 μl of a chemiluminescent substrate 3-(2'-spiroadamantane)-4-methoxy-4-(3"-phosphoryloxy)phenyl-1,2-dioxetane·disodium salt (AMPPD) was added to the resulting rinsed solution, for reaction at 37° C. for 5 minutes, to assay the luminescence with a luminometer. The assay was practically conducted with a full-automatic chemiluminescent immunoassay apparatus, Lumipulse ƒ (manufactured by Fujirebio Inc.).

The above test was carried out by using combinations of four antibody-bound particles individually bound with the YAM24-12 antibody, the YAM24-7 antibody, the YAM24-9 antibody and the p24-21 antibody and four ALP-labeled antibodies individually labeled with the YAM24-12 antibody, the YAM24-7 antibody, the YAM24-9 antibody and the p24-21 antibody. In total, 16 types of such tests were conducted.

Figure 2:
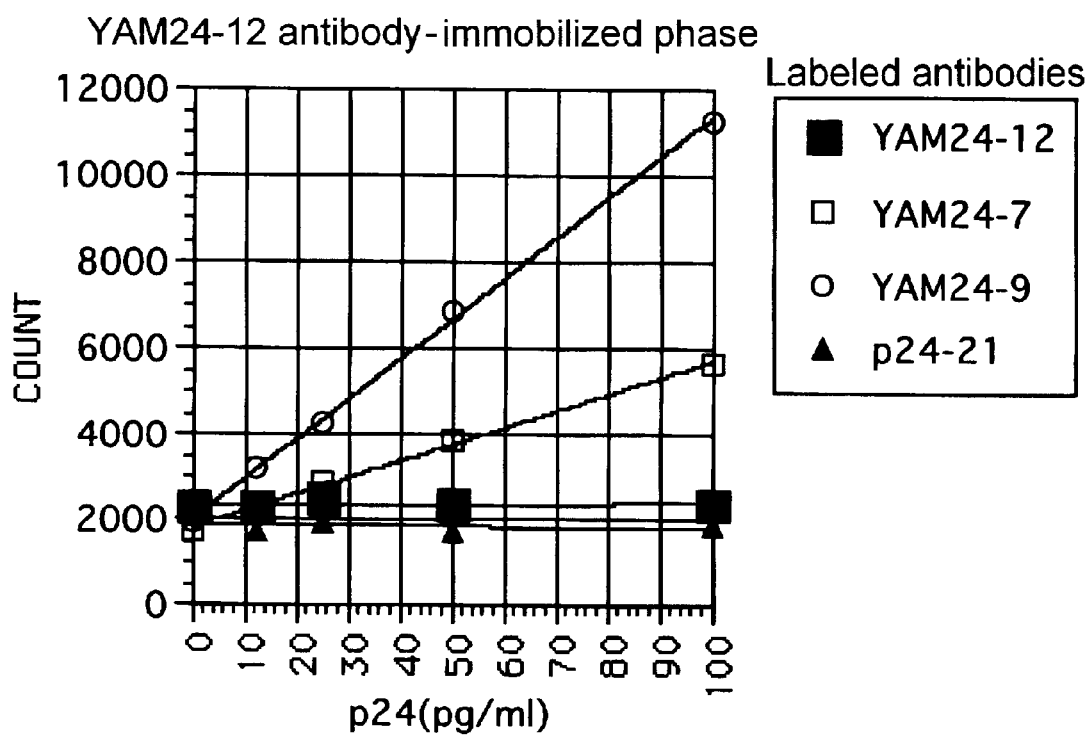
FIG. 2 shows the results of combinations of the YAM24-12 antibody-immobilized phase and various labeled antibodies.
Figure 3:
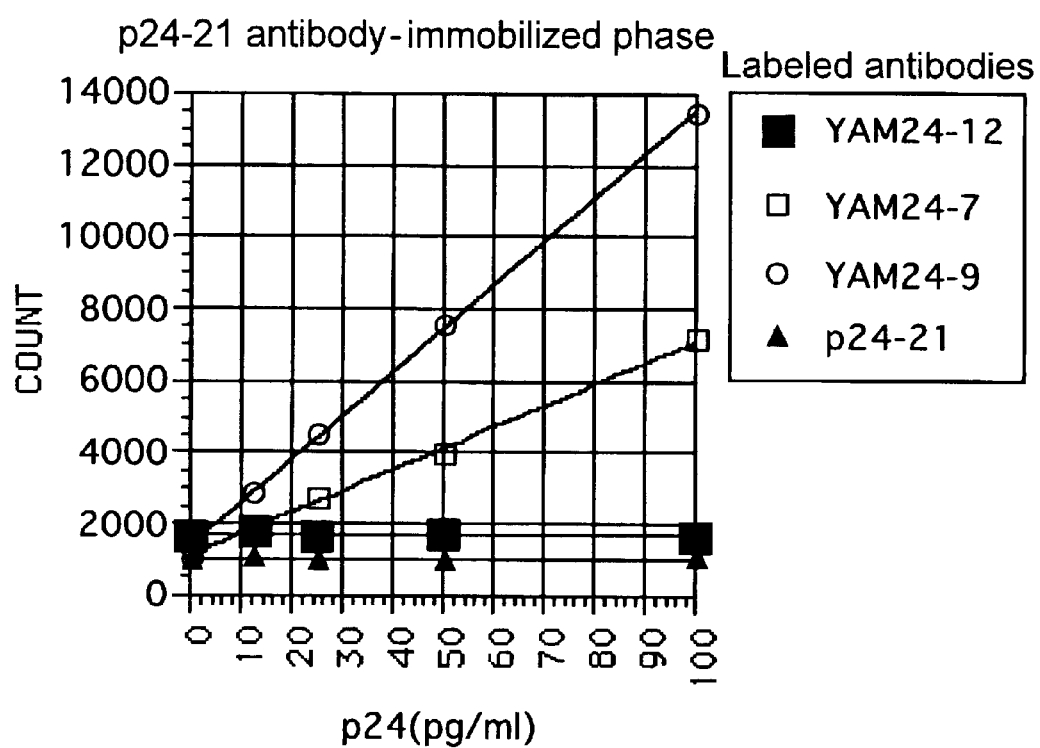
FIG. 3 shows the results of combinations of the p24-12 antibody-immobilized phase and various labeled antibodies.
Figure 4:
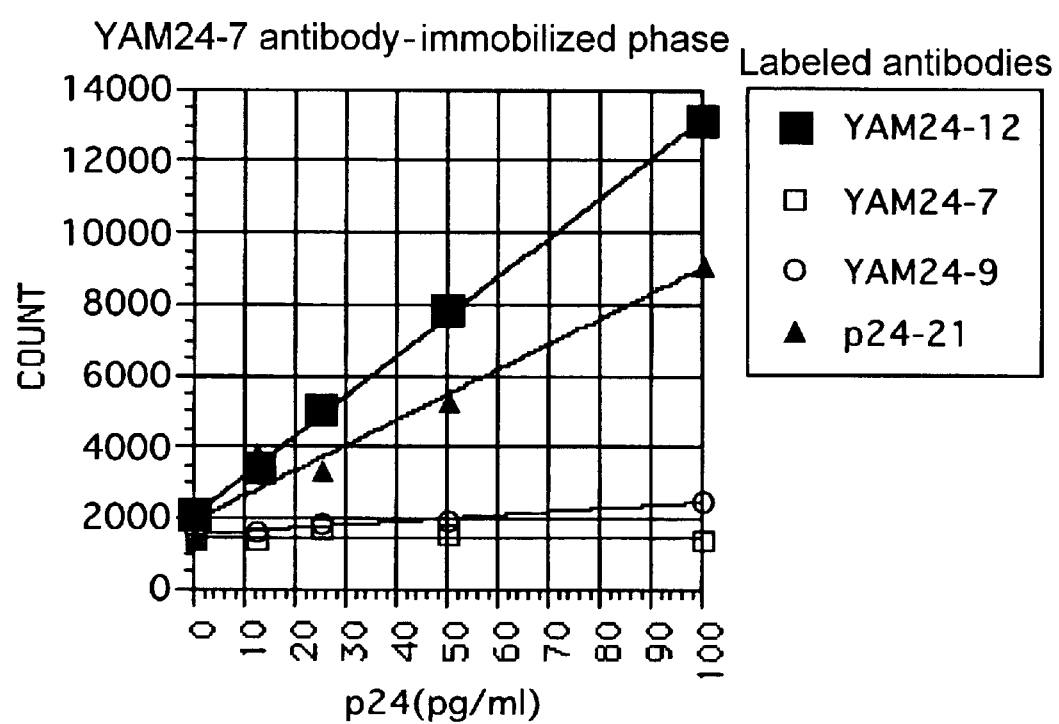
FIG. 4 shows the results of combinations of the YAM24-7 antibody-immobilized phase and various labeled antibodies.
Figure 5:
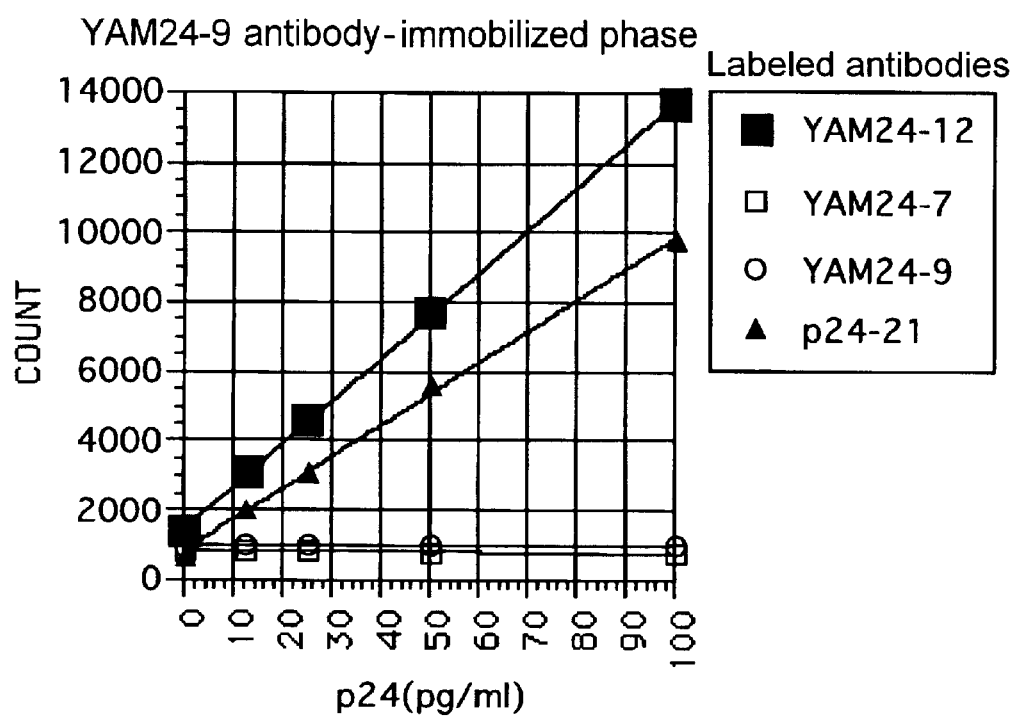
FIG. 5 shows the results of combinations of the YAM24-9 antibody-immobilized phase and various labeled antibodies.

The results of the combination tests are shown in FIGS. 2 to 5. The results of the combination tests of these antibodies show that the p24 antigen can be assayed by using only the labeled YAM24-7 antibody and YAM24-9 antibody when the YAM24-12 antibody is used on an immobilized phase, but the p24 antigen could never be assayed with almost no reaction observed, by using the labeled YAM24-12 antibody and p24-21 antibody (FIG. 2). The same results were recovered when the p24-21 antibody was used on an immobilized phase (FIG. 3). Alternatively, the p24 antigen can be assayed by using only the labeled YAM24-12 antibody and p24-21 antibody when the YAM24-7 antibody (FIG. 4) or the YAM24-9 antibody (FIG. 5) is used on an immobilized phase, but the p24 antigen could never be assayed with almost no reaction observed, by using the labeled YAM24-7 antibody and YAM24-9 antibody.

Because sandwich methods comprising sandwiching antigen with antibodies are used for the assay systems, no reaction is observed when a combination of antibodies recognizing the same epitope is used. The aforementioned results therefore indicate that the four monoclonal antibodies can be classified in a group of the YAM24-12 antibody and p24-21 antibody and a group of the YAM24-7 antibody and the YAM24-9 antibody. It is suggested that the antibodies in the same groups recognize the same epitope sites or therearound.

EXAMPLE 7

Preparation of Anti-p24 Polyclonal Antibodies

As immunogens, use was made of p24abc prepared in Example 2 and natural p24 antigen purified in Example 3; and they were mixed with the complete Freund' adjuvant at equal quantities. The natural antigen was from two rabbits, while p24abc was from four rabbits; 300 $\mu$g of each of the emulsified antigens was used for subcutaneous immunization. Every one to two weeks, additional boosters were effected seven times in total; after it was confirmed that the antibody titer was increased by micro-Ouchterlony method, whole blood was drawn. The serum was separated by centrifugation; the individual anti-sera were defined as follows: the anti-sera were defined as R-1 and R-2 when the natural p24 antigen was used; the anti-sera were defined as R-3, R-4, R-5 and R-6 when the recombinant antigen was used. Then, these anti-sera, namely R-1 to R-6, were individually purified on an affinity column Sepharose 4B immobilized with p24abc and were thus defined as anti-p24 polyclonal antibodies R-1 to R-6.

EXAMPLE 8

Assaying with ALP-labeled Anti-p24 Polyclonal Antibodies (1) Preparation of ALP-labeled Anti-p24 Polyclonal Antibodies The anti-p24 polyclonal antibody R-1 prepared in Example 7 was adjusted to a concentration of 2.0 mg/ml; 0.81 ml of the resulting solution was added to a column G-25 (manufactured by Pharmacia, Co.) equilibrated with 0.1 M citrate buffer, pH 3.5, for substitution with the buffer. 24.6 $\mu$l of 329 $\mu$g/ml pepsin solution was added to the resulting solution, which was then left to stand at 37° C. for one hour and adjusted to pH around neutrality by using Tris-HCl buffer; and the resulting solution was added to Superdex 200 column (manufactured by Pharmacia, Co.), for purification by gel filtration. The single peak of the resulting fraction at the absorbance at 280 nm was pooled, which was defined as anti-p24 polyclonal antibody F(ab')$_2$ fragment.

To 1.45 ml of the F(ab') 2 fragment solution (567 $\mu$g/ml) was added 76.3 $\mu$l of 0.2 M 2-MEA solution, and the resulting mixture was left to stand at 37° C. for 4 hours for reduction treatment. The resulting solution was added to the G-25column to discard 2-MEA, to recover then the anti-p24 polyclonal antibody Fab' fragment.

1 ml of 10 mg/ml ALP solution at a high specific activity was added to G-25 equilibrated with 0.1 M phosphate buffer, pH 6.3, for substitution with the buffer. To the resulting solution was added 53.5 $\mu$l of 10 mg/ml GMBS dimethylformamide solution, and the resulting mixture was left to stand at 37° C. for one hour for reaction. The solution was added to a G-25 column equilibrated with 0.1 M phosphate buffer, pH 7.0, to discard excess GMBS to prepare maleimidated ALP.

The previously prepared anti-p24 polyclonal YAM24-12 antibody Fab' fragment solution of 2.5 ml and the maleimidated ALP solution of 608 $\mu$l were mixed together and left to stand overnight at room temperature, to prepare ALP-labeled antibody, to which was added 31 $\mu$l of 1M 2-MEA solution. The resulting mixture was left to stand at 37° C. for one hour, to block excess maleimide groups, which was then added to Superdex 200 column for purification. Among some peaks at the absorbance at 280 nm, a peak of a molecular weight at a ratio of Fab': ALP being 1:1 was pooled and defined as purified ALP-labeled anti-p24 polyclonal antibody R-1.

The anti-p24 polyclonal antibodies R-2 to R-6 were prepared as ALP-labeled anti-p24 polyclonal antibodies R-2 to R-6 by the same method.

(2) Assay with Combinations of Labeled Polyclonal Antibodies and Monoclonal Antibodies on Immobilized Phase The particles bound with the YAM24-12 antibody, YAM24-7 antibody, YAM24-9 antibody and p24-21 antibody prepared in Example 6 (1) was adjusted to a concentration of 0.15 mg/ml; to 0.25 ml thereof were added 50 $\mu$l each of the inactivated cultured HIV antigen solution at p24 antigen concentrations of 0, 12.5, 25, 50 and 100 pg/ml, for reaction at 37° C. for 10 minutes. After rinsing with a magnet, 0.25 ml of a solution of the ALP-labeled polyclonal antibody R-1 prepared in Example 8 (1) after dilution to 1.0 $\mu$g/ml, was added to the resulting rinsed solution, for reaction at 37° C. for another 10 minutes. After rinsing with a magnet, 200 $\mu$l of AMPPD was added to the resulting rinsed solution, for reaction at 37° C. for 5 minutes, to assay the luminescence with a luminometer. The assay was conducted with a full-automatic chemiluminescent immunoassay apparatus, Lumipulse ƒ (manufactured by Fujirebio Inc.).

Figure 6:
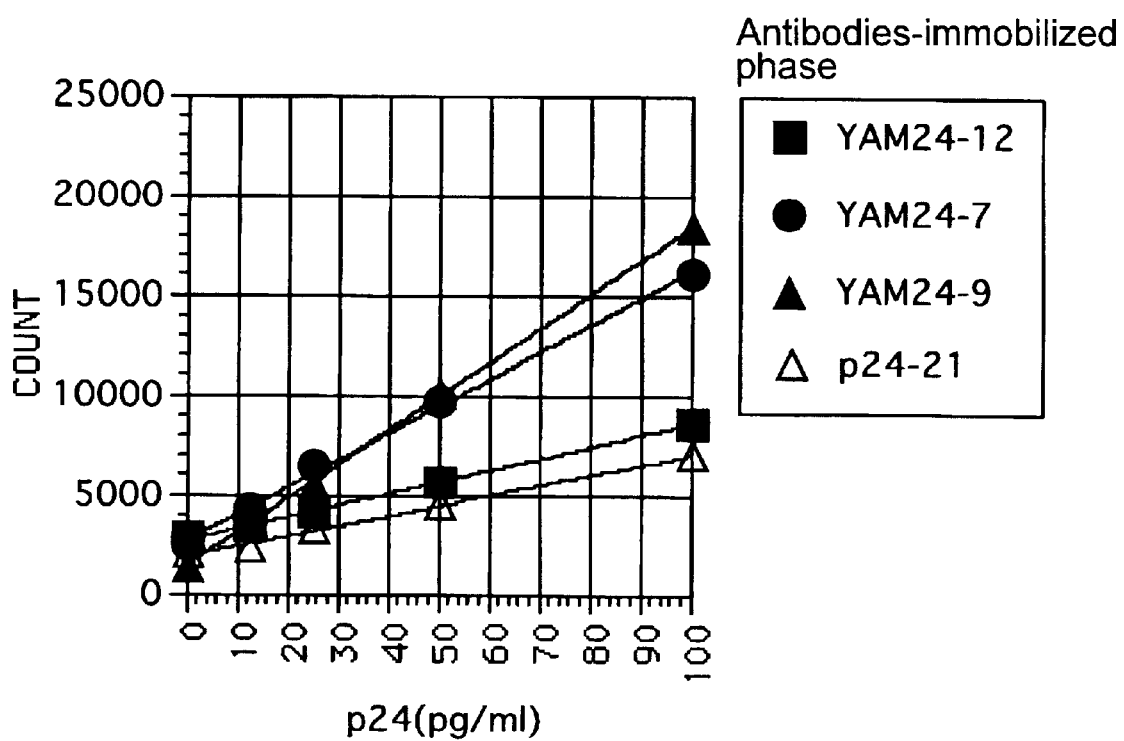
FIG. 6 shows the results of combinations of labeled polyclonal antibodies and various immobilized phase monoclonal antibodies.

The results are shown in FIG. 6. As shown in FIG. 6, the slope of the standard curve was large when the YAM24-7 antibody and YAM24-9 antibody were used for the immobilized phase, with the resultant high sensitivity. Alternatively, the slope was small when the YAM24-12 antibody and p24-21 antibody were used, with the resultant sensitivity at about 30% of the sensitivities of the YAM24-7 and YAM24-9 antibodies used.

The same experiment was conducted by using the ALP-labeled anti-p24 polyclonal antibodies R-2 to R-6, but the reactivities thereof with the antibodies YAM24-12, YAM24-7, YAM24-9 and p24-21 were at the same level as that of the ALP-labeled anti-p24 polyclonal antibody R-1.

These results are interpreted in the same manner in the case of the results in Example 6. It was thus determined that the principal recognition sites of the polyclonal antibodies R-1 to R-6 belonged to the same group as those of the YAM24-12 antibody and p24-21 antibody. Polyclonal antibodies are essentially considered as a group of antibodies recognizing plural epitopes when an antigen has wide epitopes. In this example, many of the antibodies recognize the same recognition site as that of the p24-21 antibody, namely the C-terminal region of the p24 antigen, but never include almost any antibody with a recognition site competitive to those of the antibodies YAM24-7 and 24-9.

(3) Preparation of ALP-labeled Anti-p24 Polyclonal Antibodies

Because all the principal recognition sites of the polyclonal antibodies prepared in Example 7 resided in the C-terminal region of the p24 antigen, the anti-p24 polyclonal antibodies R-3, R-4, R-5 and R-6 were pooled, which were then labeled with ALP in the same manner as described in Example 8 (1), for subsequent use as ALP-labeled anti-p24 polyclonal antibodies in the following experiments.

EXAMPLE 9

Assay of p24 Antigen by Using the Monoclonal Antibodies Anti-p24N1-9 Antibody and p24N3-3 Antibody and the Polyclonal Antibodies (1) Preparation of p24N1-9 antibody- and p24N3-3 Antibody-bound Particles To 0.075 ml of 50 mg/ml ferrite particle (manufactured by Nippon Paint Co.) was added 14 μl of a 7.15 mg/ml solution of the monoclonal antibody p24N1-9 antibody prepared in Example 4, followed by agitation and subsequent agitation at 25° C. in an end-over-end fashion for one hour. The ferrite particle was collected magnetically with a magnet to discard the supernatant; then, the resulting particle was rinsed twice in 0.4% NaCl solution, followed by addition of 2 ml of 50 mM carbonate buffer, pH 9.0 containing 2% BSA, subsequent agitation and further agitation overnight at 37° C. in an end-over-end fashion, to prepare p24N1-9 antibody-bound particle.

In the same manner, p24N3-3 antibody-bound particle was prepared by using 12 μl of the p24N3-3 antibody (8.41 mg/ml).

(2) Assay of p24 Standard Antigen

Figure 7:
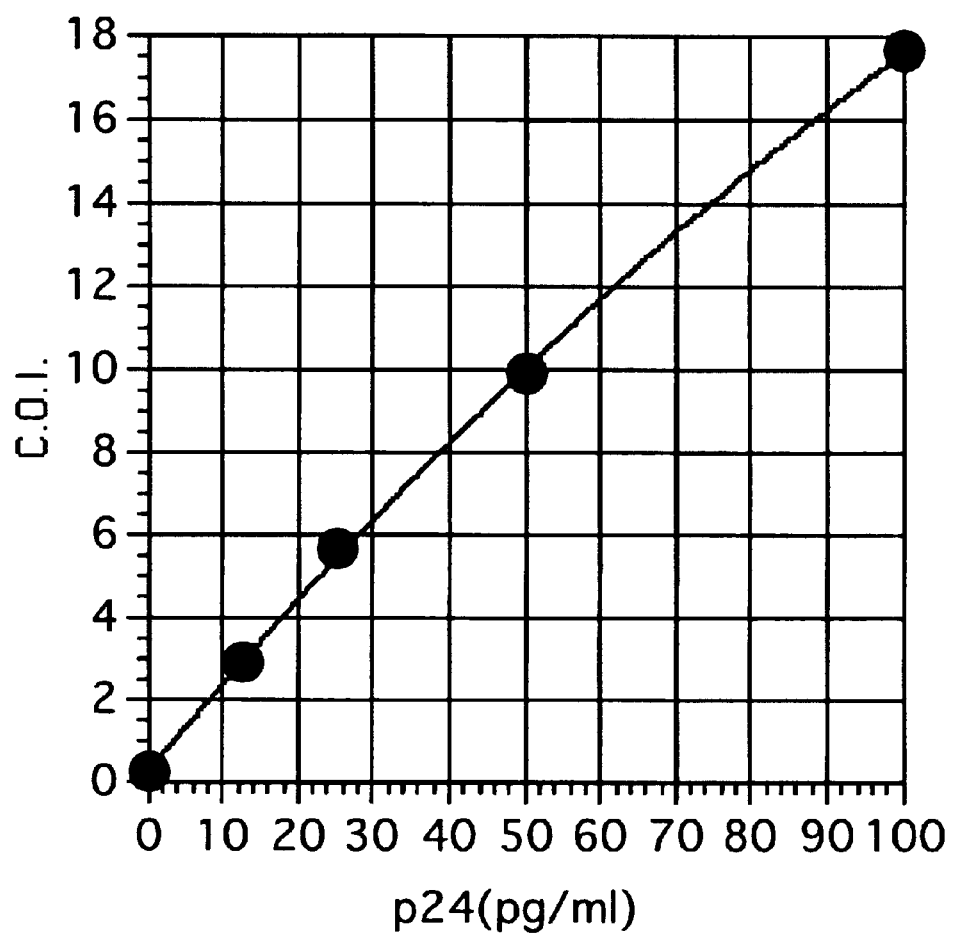
FIG. 7 shows the assay sensitivity (in the whole range) of the HIV-1p24 antigen according to the inventive method.
Figure 8:
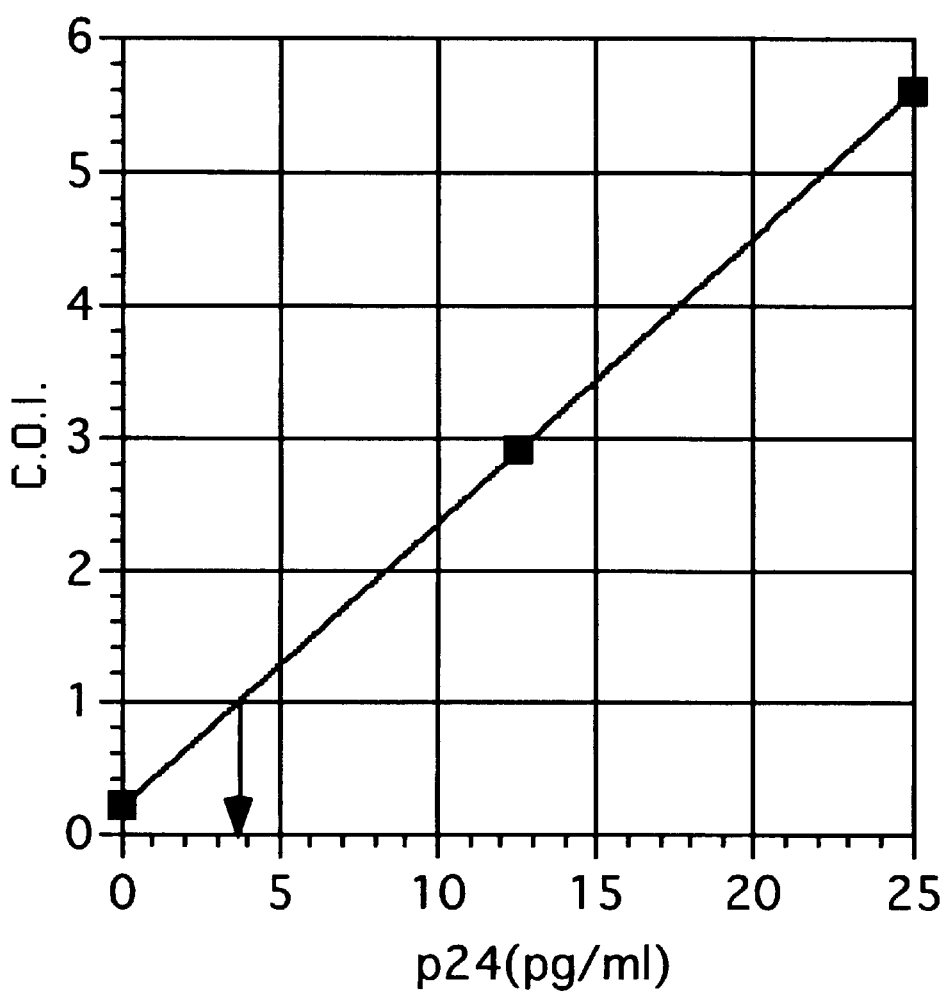
FIG. 8 shows the assay sensitivity (in the low concentration range) of the HIV-1p24 antigen according to the inventive method.

The two antibody-bound particles prepared in Example 9 (1) were adjusted to a concentration of 1.875 mg/ml; 10 μl each was placed, from which only the particle supernatant was discarded, followed by addition of 250 μl of a reaction solution (50 mM Tris buffer, pH 7.2, 0.15 M NaCl, 2% BSA, 1 mM ethylenediaminetetraacetate, 0.1% sodium azide) and 100 μl of the HIV-1p24 standard antigen solution (manufactured by ABBOTT) at p24 antigen concentrations of 0, 12.5, 25, 50 and 100 pg/ml, for reaction at 37° C. for 10 minutes. After rinsing with a magnet, 0.25 ml of a solution of the purified ALP-labeled anti-p24 polyclonal antibody prepared in Example 8 (3) after dilution to 1.0 μg/ml was added to the resulting particle, for reaction at 37° C. for another 10 minutes. After rinsing with a magnet, AMPPD of 200 μl was added for reaction at 37° C. for 5 minutes. The luminescence was assayed with a luminometer. The assay was practically conducted with a full-automatic chemiluminescent immunoassay apparatus, Lumipulse ƒ (manufactured by Fujirebio Inc.). The results are shown in FIGS. 7 and 8. On the longitudinal axis, cut-off-index values (C.O.I.) are shown when the cut-off value is 1.0. At 1.0 of the C.O.I. value, the concentration of the p24 antigen was about 4 μg/ml.

EXAMPLE 10

Comparison of Sensitivity with Those of Other Existing Assay Systems (1) Assay with HIV Antigen·EIA "ABBOTT"

Figure 9:
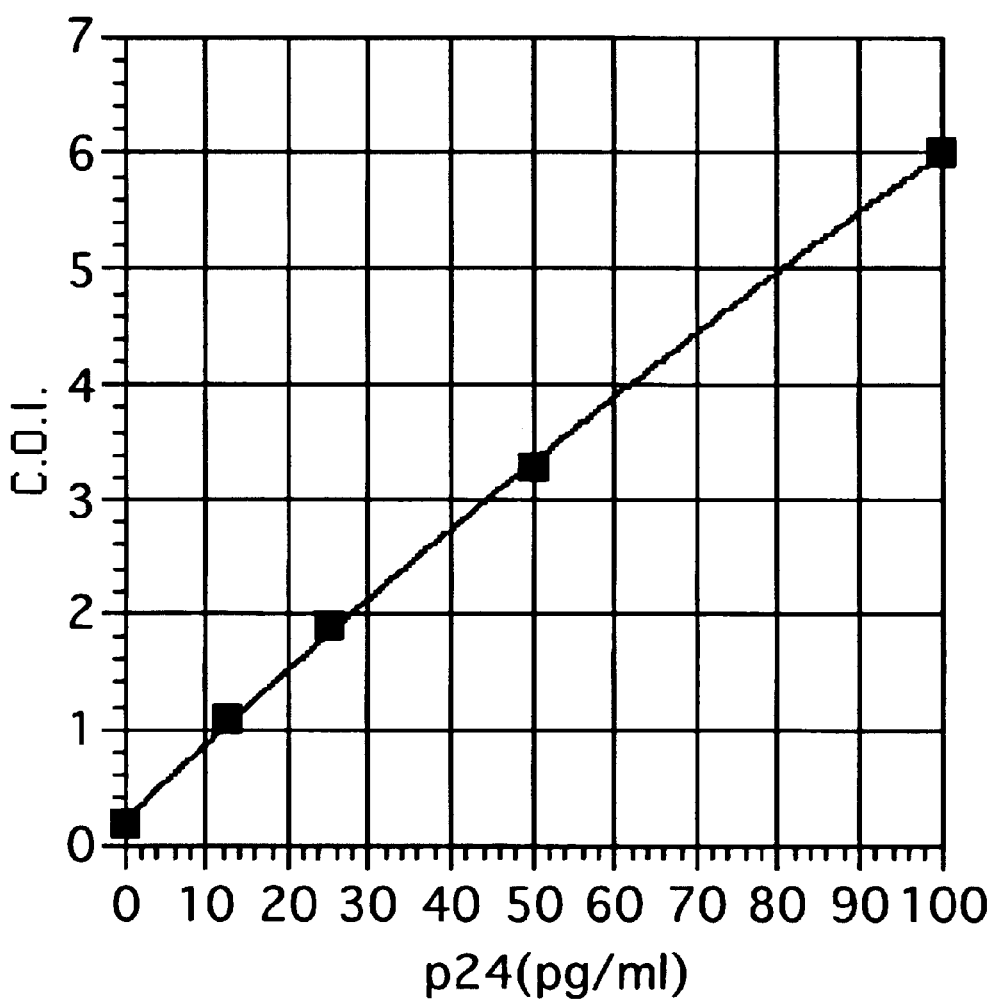
FIG. 9 shows the assay sensitivity (in the whole range) of the HIV-1p24 antigen by the existing assay method.
Figure 10:
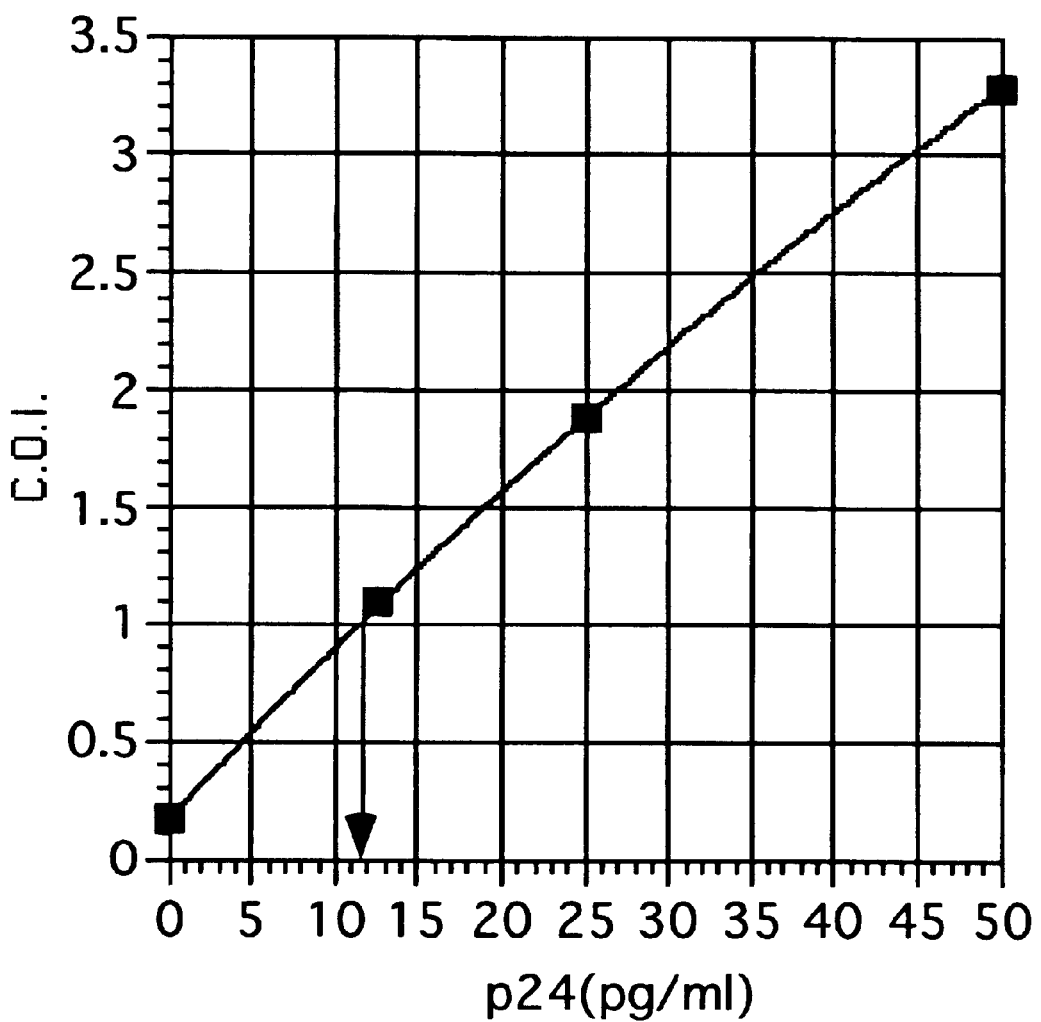
FIG. 10 shows the assay sensitivity (in the low concentration range) of the HIV-1p24 antigen by the existing assay method.

As an existing assay system, HIV Antigen·EIA "ABBOTT"kit was used. The assay was conducted according to the instructions attached. More specifically, 200 μl of each of the HIV-1p24 standard antigen solution used in Example 9 (2) and the control sample was divided in a reaction tray, to which was added the HIV antibody bead for reaction at 40° C. for 3 hours. The control sample was used as follows; a sample dilution solution of 20 μl was added to the control sample of 200 μl. After rinsing of the bead, 200 μl of the HIV antibody was added for reaction at 40° C. for another one hour; after rinsing of the bead, 200 μl of the anti-IgG antibody-peroxidase was added for reaction at 40° C. for one hour. After rinsing the resulting mixture, 300 μl of o-phenylenediamine dichloride salt solution as a peroxidase substrate was added for reaction at 15 to 30° C. for 30 minutes; and thereafter, 1 N sulfuric acid was added to terminate the reaction. The absorbance of the solution at 492 nm was assayed. The results are shown in FIGS. 9 and 10. The cut-off value of the assay kit is defined as the numerical value of the mean absorbance of three negative controls plus 0.05. On the longitudinal axis, the cut-off-index values (C.I.O.) are shown when the cut-off value is defined as 1.0. Thus, the concentration of the p24 antigen at the cut-off value was about 12 pg/ml.

The p24 antigen concentration at the cut-off value in the assay system defined in Example 9 (2) was about 4 pg/ml; and the p24 antigen concentration at the cut-off value in the HIV Antigen·EIA "ABBOTT" defined in the present Example was about 12 pg/ml. Thus, the difference was about 3-fold.

The ABBOTT kit requires a sample volume of 200 μl, a first reaction time of 3 hours, a second reaction time of one hour, a third reaction time of one hour and an enzyme reaction time of 30 minutes. On contrast, the present assay system requires a sample volume of 100 μl, a first reaction time of 10 minutes, a second reaction time of 10 minutes and an enzyme reaction time of 5 minutes. Comparison of the two assay systems indicates that the present assay system requires 1/2-fold sample volume and 1/12-fold immunoreaction time at 3-fold assay sensitivity. Because sensitivity is influenced by sample volume and immunoreaction time, the assay sensitivity of the present assay system is higher than that of the existing assay method, although the sample volume is less and the immunoreaction time is short according to the present assay system. Hence, the assay system is indicated to be a highly sensitive HIV-1p24 assay system never conventionally found.

In accordance with the invention, the assay method and reagent of the HIV-1p24 antigen can be provided, which enable more highly sensitive assay of the HIV-1p24 antigen than conventionally.

What is claimed is:

1. A sandwich immunoassay method for HIV-1p24 antigen, using at least one polyclonal antibody recognizing the HIV-1p24 antigen and at least two monoclonal antibodies recognizing HIV-1p24 antigen, wherein the principal recognition site of the polyclonal antibody is the C-terminal region of the HIV-1p24 antigen and wherein one of the at least two monoclonal antibodies recognizing the HIV-1p24 antigen recognizes the N-terminus and said monoclonal antibody is p24N1-9 and another of the at least two monoclonal antibodies recognizing the HIV-1p24 antigen recognizes an intermediate site of the HIV-1p24 antigen.

2. A sandwich immunoassay method for HIV-1p24 antigen, using at least one polyclonal antibody recognizing the HIV-1p24 antigen and at least two monoclonal antibodies recognizing HIV-1p24 antigen, wherein the principal recognition site of the polyclonal antibody is the C-terminal region of the HIV-1p24 antigen and wherein one of the at least two monoclonal antibodies recognizing the HIV-1p24 antigen recognizes the N-terminus of the HIV-1p24 antigen and another of the at least two monoclonal antibodies recognizing the HIV-1p24 antigen recognizes an intermediate site of the HIV-1p24 antigen and said antibody is p24N3-3.

* * * * *

SEQUENCE LISTING

<160> NUMBER OF SEQ ID NOS: 32

<210> SEQ ID NO 1

-continued

```
<211> LENGTH: 879
<212> TYPE: DNA
<213> ORGANISM: Human immunodeficiency virus type 1
<220> FEATURE:
<221> NAME/KEY: CDS
<222> LOCATION: (1)..(876)

<400> SEQUENCE: 1
```

| | | | | | | | | | | | | | | | | |
|---|---|---|---|---|---|---|---|---|---|---|---|---|---|---|---|---|
| atg | acc | atg | att | acg | cca | agc | ttg | gct | gca | tgg | gta | aaa | gta | ata | gaa | 48 |
| Met | Thr | Met | Ile | Thr | Pro | Ser | Leu | Ala | Ala | Trp | Val | Lys | Val | Ile | Glu | |
| 1 | | | | 5 | | | | | 10 | | | | | 15 | | |
| gaa | aag | gct | ttc | agc | cca | gaa | gtg | ata | ccc | atg | ttt | tca | gca | tta | tca | 96 |
| Glu | Lys | Ala | Phe | Ser | Pro | Glu | Val | Ile | Pro | Met | Phe | Ser | Ala | Leu | Ser | |
| | | | | 20 | | | | | 25 | | | | | 30 | | |
| gaa | gga | gcc | acc | cca | caa | gat | tta | aat | acc | atg | cta | aac | aca | gtg | ggg | 144 |
| Glu | Gly | Ala | Thr | Pro | Gln | Asp | Leu | Asn | Thr | Met | Leu | Asn | Thr | Val | Gly | |
| | | | 35 | | | | | 40 | | | | | 45 | | | |
| gga | cat | caa | gca | gcc | atg | caa | atg | tta | aaa | gag | acc | atc | aat | gag | gaa | 192 |
| Gly | His | Gln | Ala | Ala | Met | Gln | Met | Leu | Lys | Glu | Thr | Ile | Asn | Glu | Glu | |
| | | 50 | | | | | 55 | | | | | 60 | | | | |
| gct | gca | gaa | tgg | gat | aga | gtg | cat | cca | gtg | cat | gca | ggg | cct | att | gca | 240 |
| Ala | Ala | Glu | Trp | Asp | Arg | Val | His | Pro | Val | His | Ala | Gly | Pro | Ile | Ala | |
| 65 | | | | | 70 | | | | | 75 | | | | | 80 | |
| cca | ggc | cag | atg | aga | gaa | cca | agg | gga | agt | gat | ata | gca | gga | act | act | 288 |
| Pro | Gly | Gln | Met | Arg | Glu | Pro | Arg | Gly | Ser | Asp | Ile | Ala | Gly | Thr | Thr | |
| | | | | 85 | | | | | 90 | | | | | 95 | | |
| agt | acc | ctt | cag | gaa | caa | ata | gga | tgg | atg | aca | aac | aat | cca | cct | atc | 336 |
| Ser | Thr | Leu | Gln | Glu | Gln | Ile | Gly | Trp | Met | Thr | Asn | Asn | Pro | Pro | Ile | |
| | | | 100 | | | | | 105 | | | | | 110 | | | |
| cca | gta | gga | gaa | atc | tat | aaa | aga | tgg | ata | atc | ctg | gga | tta | aat | aaa | 384 |
| Pro | Val | Gly | Glu | Ile | Tyr | Lys | Arg | Trp | Ile | Ile | Leu | Gly | Leu | Asn | Lys | |
| | | | 115 | | | | | 120 | | | | | 125 | | | |
| ata | gta | aga | atg | tat | agt | cct | gtt | agt | att | ctg | gac | ata | aga | caa | gga | 432 |
| Ile | Val | Arg | Met | Tyr | Ser | Pro | Val | Ser | Ile | Leu | Asp | Ile | Arg | Gln | Gly | |
| | | 130 | | | | | 135 | | | | | 140 | | | | |
| cca | aag | gaa | ccc | ttt | aga | gac | tat | gta | gat | cgg | ttc | tat | aaa | act | tta | 480 |
| Pro | Lys | Glu | Pro | Phe | Arg | Asp | Tyr | Val | Asp | Arg | Phe | Tyr | Lys | Thr | Leu | |
| 145 | | | | | 150 | | | | | 155 | | | | | 160 | |
| aga | gcc | gag | caa | gct | tca | cag | gag | gta | aaa | aat | tgg | atg | aca | gaa | acc | 528 |
| Arg | Ala | Glu | Gln | Ala | Ser | Gln | Glu | Val | Lys | Asn | Trp | Met | Thr | Glu | Thr | |
| | | | | 165 | | | | | 170 | | | | | 175 | | |
| ttg | ttg | gtc | caa | aat | gcg | aac | cca | gac | tgt | aag | act | att | cta | aaa | gca | 576 |
| Leu | Leu | Val | Gln | Asn | Ala | Asn | Pro | Asp | Cys | Lys | Thr | Ile | Leu | Lys | Ala | |
| | | | 180 | | | | | 185 | | | | | 190 | | | |
| tta | gga | cca | gca | gct | aca | cta | gaa | gaa | atg | atg | aca | gca | tgt | cag | gga | 624 |
| Leu | Gly | Pro | Ala | Ala | Thr | Leu | Glu | Glu | Met | Met | Thr | Ala | Cys | Gln | Gly | |
| | | | 195 | | | | | 200 | | | | | 205 | | | |
| gtg | ggg | gga | ccc | ggc | cat | aag | gca | aga | gtg | ttg | gct | gaa | gca | atg | agc | 672 |
| Val | Gly | Gly | Pro | Gly | His | Lys | Ala | Arg | Val | Leu | Ala | Glu | Ala | Met | Ser | |
| | | 210 | | | | | 215 | | | | | 220 | | | | |
| caa | gta | aca | aat | tca | gct | acc | ata | atg | atg | cag | aga | ggt | aat | ttt | agg | 720 |
| Gln | Val | Thr | Asn | Ser | Ala | Thr | Ile | Met | Met | Gln | Arg | Gly | Asn | Phe | Arg | |
| 225 | | | | | 230 | | | | | 235 | | | | | 240 | |
| aac | caa | aaa | aaa | act | gtt | aag | tgt | ttc | aat | tgt | ggc | aaa | gaa | ggg | cac | 768 |
| Asn | Gln | Lys | Lys | Thr | Val | Lys | Cys | Phe | Asn | Cys | Gly | Lys | Glu | Gly | His | |
| | | | | 245 | | | | | 250 | | | | | 255 | | |
| ata | gcc | aaa | aat | tgc | agg | gcc | cct | agg | aaa | aag | ggc | tgt | tgg | aaa | tgt | 816 |
| Ile | Ala | Lys | Asn | Cys | Arg | Ala | Pro | Arg | Lys | Lys | Gly | Cys | Trp | Lys | Cys | |
| | | | 260 | | | | | 265 | | | | | 270 | | | |
| gga | aag | gaa | gga | cac | caa | atg | aaa | gat | tgt | act | gag | aga | cag | gct | aat | 864 |
| Gly | Lys | Glu | Gly | His | Gln | Met | Lys | Asp | Cys | Thr | Glu | Arg | Gln | Ala | Asn | |

```
            275                 280                 285
ttt tta ggg aac tga                                                        879
Phe Leu Gly Asn
    290

<210> SEQ ID NO 2
<211> LENGTH: 292
<212> TYPE: PRT
<213> ORGANISM: Human immunodeficiency virus type 1

<400> SEQUENCE: 2

Met Thr Met Ile Thr Pro Ser Leu Ala Ala Trp Val Lys Val Ile Glu
1               5                   10                  15

Glu Lys Ala Phe Ser Pro Glu Val Ile Pro Met Phe Ser Ala Leu Ser
            20                  25                  30

Glu Gly Ala Thr Pro Gln Asp Leu Asn Thr Met Leu Asn Thr Val Gly
        35                  40                  45

Gly His Gln Ala Ala Met Gln Met Leu Lys Glu Thr Ile Asn Glu Glu
    50                  55                  60

Ala Ala Glu Trp Asp Arg Val His Pro Val His Ala Gly Pro Ile Ala
65                  70                  75                  80

Pro Gly Gln Met Arg Glu Pro Arg Gly Ser Asp Ile Ala Gly Thr Thr
                85                  90                  95

Ser Thr Leu Gln Glu Gln Ile Gly Trp Met Thr Asn Asn Pro Pro Ile
            100                 105                 110

Pro Val Gly Glu Ile Tyr Lys Arg Trp Ile Ile Leu Gly Leu Asn Lys
        115                 120                 125

Ile Val Arg Met Tyr Ser Pro Val Ser Ile Leu Asp Ile Arg Gln Gly
    130                 135                 140

Pro Lys Glu Pro Phe Arg Asp Tyr Val Asp Arg Phe Tyr Lys Thr Leu
145                 150                 155                 160

Arg Ala Glu Gln Ala Ser Gln Glu Val Lys Asn Trp Met Thr Glu Thr
                165                 170                 175

Leu Leu Val Gln Asn Ala Asn Pro Asp Cys Lys Thr Ile Leu Lys Ala
            180                 185                 190

Leu Gly Pro Ala Ala Thr Leu Glu Glu Met Met Thr Ala Cys Gln Gly
        195                 200                 205

Val Gly Gly Pro Gly His Lys Ala Arg Val Leu Ala Glu Ala Met Ser
    210                 215                 220

Gln Val Thr Asn Ser Ala Thr Ile Met Met Gln Arg Gly Asn Phe Arg
225                 230                 235                 240

Asn Gln Lys Lys Thr Val Lys Cys Phe Asn Cys Gly Lys Glu Gly His
                245                 250                 255

Ile Ala Lys Asn Cys Arg Ala Pro Arg Lys Lys Gly Cys Trp Lys Cys
            260                 265                 270

Gly Lys Glu Gly His Gln Met Lys Asp Cys Thr Glu Arg Gln Ala Asn
        275                 280                 285

Phe Leu Gly Asn
    290

<210> SEQ ID NO 3
<211> LENGTH: 52
<212> TYPE: DNA
<213> ORGANISM: Artificial Sequence
<220> FEATURE:
<223> OTHER INFORMATION: Primer 24F1 based on HIV
```

-continued

```
<400> SEQUENCE: 3
caacatatga ccatgattac gccaagcttg gctgcatggg taaaagtaat ag           52

<210> SEQ ID NO 4
<211> LENGTH: 31
<212> TYPE: DNA
<213> ORGANISM: Artificial Sequence
<220> FEATURE:
<223> OTHER INFORMATION: Primer 24F2 based on HIV

<400> SEQUENCE: 4
caaagaattc gaacaaatag gatggatgac a                                  31

<210> SEQ ID NO 5
<211> LENGTH: 31
<212> TYPE: DNA
<213> ORGANISM: Artificial Sequence
<220> FEATURE:
<223> OTHER INFORMATION: Primer 24F3 based on HIV

<400> SEQUENCE: 5
caaagaattc gaaatgatga cagcatgtca g                                  31

<210> SEQ ID NO 6
<211> LENGTH: 57
<212> TYPE: DNA
<213> ORGANISM: Artificial Sequence
<220> FEATURE:
<223> OTHER INFORMATION: Primer 24F+1 based on HIV

<400> SEQUENCE: 6
caagaattcc ctatagtgca gaacatccag gggcaaatgg tacatcaggc catatca      57

<210> SEQ ID NO 7
<211> LENGTH: 57
<212> TYPE: DNA
<213> ORGANISM: Artificial Sequence
<220> FEATURE:
<223> OTHER INFORMATION: Primer 24F+2 based on HIV

<400> SEQUENCE: 7
tggtacatca ggccatatca cctagaactt taaatgcatg ggtaaaagta atagaag      57

<210> SEQ ID NO 8
<211> LENGTH: 30
<212> TYPE: DNA
<213> ORGANISM: Artificial Sequence
<220> FEATURE:
<223> OTHER INFORMATION: Primer 24R1 based on HIV

<400> SEQUENCE: 8
gaactcgagc tgaagggtac tagtagttcc                                    30

<210> SEQ ID NO 9
<211> LENGTH: 30
<212> TYPE: DNA
<213> ORGANISM: Artificial Sequence
<220> FEATURE:
<223> OTHER INFORMATION: Primer 24R2 based on HIV

<400> SEQUENCE: 9
gttctcgagt tctagtgtag ctgctggtcc                                    30

<210> SEQ ID NO 10
<211> LENGTH: 35
```

```
<212> TYPE: DNA
<213> ORGANISM: Artificial Sequence
<220> FEATURE:
<223> OTHER INFORMATION: Primer 24R3 based on HIV

<400> SEQUENCE: 10
gttggatcct tagttcccta aaaaattagc ctgtc                          35

<210> SEQ ID NO 11
<211> LENGTH: 30
<212> TYPE: DNA
<213> ORGANISM: Artificial Sequence
<220> FEATURE:
<223> OTHER INFORMATION: Primer 25F based on HIV

<400> SEQUENCE: 11
caacatatgc ctgtacaaca gacaggcggt                                30

<210> SEQ ID NO 12
<211> LENGTH: 33
<212> TYPE: DNA
<213> ORGANISM: Artificial Sequence
<220> FEATURE:
<223> OTHER INFORMATION: Primer 25R based on HIV

<400> SEQUENCE: 12
cttctcgagt tatagtctgg cttttttggcc tgg                           33

<210> SEQ ID NO 13
<211> LENGTH: 12
<212> TYPE: PRT
<213> ORGANISM: Human immunodeficiency virus type 1

<400> SEQUENCE: 13

Pro Ala Ala Thr Leu Glu Glu Met Met Thr Ala Cys
1               5                   10

<210> SEQ ID NO 14
<211> LENGTH: 27
<212> TYPE: PRT
<213> ORGANISM: Human immunodeficiency virus type 1

<400> SEQUENCE: 14

Pro Ile Val Gln Asn Ile Gln Gly Gln Met Val His Gln Ala Ile Ser
1               5                   10                  15

Pro Arg Thr Leu Asn Ala Trp Val Lys Val Ile
            20                  25

<210> SEQ ID NO 15
<211> LENGTH: 12
<212> TYPE: PRT
<213> ORGANISM: Human immunodeficiency virus type 1

<400> SEQUENCE: 15

Thr Thr Ser Thr Leu Gln Glu Gln Ile Gly Trp Met
1               5                   10

<210> SEQ ID NO 16
<211> LENGTH: 879
<212> TYPE: DNA
<213> ORGANISM: Human immunodeficiency virus type 1
<220> FEATURE:
<221> NAME/KEY: CDS
<222> LOCATION: (1)..(876)

<400> SEQUENCE: 16
```

```
atg acc atg att acg cca agc ttg gct gca tgg gta aaa gta ata gaa      48
Met Thr Met Ile Thr Pro Ser Leu Ala Ala Trp Val Lys Val Ile Glu
1               5                   10                  15 gaa aag gct ttc agc cca gaa gtg ata ccc atg ttt tca gca tta tca      96
Glu Lys Ala Phe Ser Pro Glu Val Ile Pro Met Phe Ser Ala Leu Ser
            20                  25                  30 gaa gga gcc acc cca caa gat tta aat acc atg cta aac aca gtg ggg     144
Glu Gly Ala Thr Pro Gln Asp Leu Asn Thr Met Leu Asn Thr Val Gly
        35                  40                  45 gga cat caa gca gcc atg caa atg tta aaa gag acc atc aat gag gaa     192
Gly His Gln Ala Ala Met Gln Met Leu Lys Glu Thr Ile Asn Glu Glu
    50                  55                  60 gct gca gaa tgg gat aga gtg cat cca gtg cat gca ggg cct att gca     240
Ala Ala Glu Trp Asp Arg Val His Pro Val His Ala Gly Pro Ile Ala
65                  70                  75                  80 cca ggc cag atg aga gaa cca agg gga agt gat ata gca gga act act     288
Pro Gly Gln Met Arg Glu Pro Arg Gly Ser Asp Ile Ala Gly Thr Thr
                85                  90                  95 agt acc ctt cag gaa caa ata gga tgg atg aca aac aat cca cct atc     336
Ser Thr Leu Gln Glu Gln Ile Gly Trp Met Thr Asn Asn Pro Pro Ile
            100                 105                 110 cca gta gga gaa atc tat aaa aga tgg ata atc ctg gga tta aat aaa     384
Pro Val Gly Glu Ile Tyr Lys Arg Trp Ile Ile Leu Gly Leu Asn Lys
        115                 120                 125 ata gta aga atg tat agt cct gtt agt att ctg gac ata aga caa gga     432
Ile Val Arg Met Tyr Ser Pro Val Ser Ile Leu Asp Ile Arg Gln Gly
    130                 135                 140 cca aag gaa ccc ttt aga gac tat gta gat cgg ttc tat aaa act tta     480
Pro Lys Glu Pro Phe Arg Asp Tyr Val Asp Arg Phe Tyr Lys Thr Leu
145                 150                 155                 160 aga gcc gag caa gct tca cag gag gta aaa aat tgg atg aca gaa acc     528
Arg Ala Glu Gln Ala Ser Gln Glu Val Lys Asn Trp Met Thr Glu Thr
                165                 170                 175 ttg ttg gtc caa aat gcg aac cca gac tgt aag act att cta aaa gca     576
Leu Leu Val Gln Asn Ala Asn Pro Asp Cys Lys Thr Ile Leu Lys Ala
            180                 185                 190 tta gga cca gca gct aca cta gaa gaa atg atg aca gca tgt cag gga     624
Leu Gly Pro Ala Ala Thr Leu Glu Glu Met Met Thr Ala Cys Gln Gly
        195                 200                 205 gtg ggg gga ccc ggc cat aag gca aga gtg ttg gct gaa gca atg agc     672
Val Gly Gly Pro Gly His Lys Ala Arg Val Leu Ala Glu Ala Met Ser
    210                 215                 220 caa gta aca aat tca gct acc ata atg atg cag aga ggt aat ttt agg     720
Gln Val Thr Asn Ser Ala Thr Ile Met Met Gln Arg Gly Asn Phe Arg
225                 230                 235                 240 aac caa aaa aaa act gtt aag tgt ttc aat tgt ggc aaa gaa ggg cac     768
Asn Gln Lys Lys Thr Val Lys Cys Phe Asn Cys Gly Lys Glu Gly His
                245                 250                 255 ata gcc aaa aat tgc agg gcc cct agg aaa aag ggc tgt tgg aaa tgt     816
Ile Ala Lys Asn Cys Arg Ala Pro Arg Lys Lys Gly Cys Trp Lys Cys
            260                 265                 270 gga aag gaa gga cac caa atg aaa gat tgt act gag aga cag gct aat     864
Gly Lys Glu Gly His Gln Met Lys Asp Cys Thr Glu Arg Gln Ala Asn
        275                 280                 285 ttt tta ggg aac taa                                                 879
Phe Leu Gly Asn
    290
```

<210> SEQ ID NO 17

```
<211> LENGTH: 292
<212> TYPE: PRT
<213> ORGANISM: Human immunodeficiency virus type 1

<400> SEQUENCE: 17

Met Thr Met Ile Thr Pro Ser Leu Ala Ala Trp Val Lys Val Ile Glu
1               5                   10                  15

Glu Lys Ala Phe Ser Pro Glu Val Ile Pro Met Phe Ser Ala Leu Ser
            20                  25                  30

Glu Gly Ala Thr Pro Gln Asp Leu Asn Thr Met Leu Asn Thr Val Gly
        35                  40                  45

Gly His Gln Ala Ala Met Gln Met Leu Lys Glu Thr Ile Asn Glu Glu
    50                  55                  60

Ala Ala Glu Trp Asp Arg Val His Pro Val His Ala Gly Pro Ile Ala
65                  70                  75                  80

Pro Gly Gln Met Arg Glu Pro Arg Gly Ser Asp Ile Ala Gly Thr Thr
                85                  90                  95

Ser Thr Leu Gln Glu Gln Ile Gly Trp Met Thr Asn Asn Pro Pro Ile
            100                 105                 110

Pro Val Gly Glu Ile Tyr Lys Arg Trp Ile Ile Leu Gly Leu Asn Lys
        115                 120                 125

Ile Val Arg Met Tyr Ser Pro Val Ser Ile Leu Asp Ile Arg Gln Gly
    130                 135                 140

Pro Lys Glu Pro Phe Arg Asp Tyr Val Asp Arg Phe Tyr Lys Thr Leu
145                 150                 155                 160

Arg Ala Glu Gln Ala Ser Gln Glu Val Lys Asn Trp Met Thr Glu Thr
                165                 170                 175

Leu Leu Val Gln Asn Ala Asn Pro Asp Cys Lys Thr Ile Leu Lys Ala
            180                 185                 190

Leu Gly Pro Ala Ala Thr Leu Glu Glu Met Met Thr Ala Cys Gln Gly
        195                 200                 205

Val Gly Gly Pro Gly His Lys Ala Arg Val Leu Ala Glu Ala Met Ser
    210                 215                 220

Gln Val Thr Asn Ser Ala Thr Ile Met Met Gln Arg Gly Asn Phe Arg
225                 230                 235                 240

Asn Gln Lys Lys Thr Val Lys Cys Phe Asn Cys Gly Lys Glu Gly His
                245                 250                 255

Ile Ala Lys Asn Cys Arg Ala Pro Arg Lys Lys Gly Cys Trp Lys Cys
            260                 265                 270

Gly Lys Glu Gly His Gln Met Lys Asp Cys Thr Glu Arg Gln Ala Asn
        275                 280                 285

Phe Leu Gly Asn
    290

<210> SEQ ID NO 18
<211> LENGTH: 348
<212> TYPE: DNA
<213> ORGANISM: Human immunodeficiency virus type 1
<220> FEATURE:
<221> NAME/KEY: CDS
<222> LOCATION: (1)..(345)

<400> SEQUENCE: 18 atg acc atg att acg cca agc ttg gct gca tgg gta aaa gta ata gaa      48
Met Thr Met Ile Thr Pro Ser Leu Ala Ala Trp Val Lys Val Ile Glu
1               5                   10                  15 gaa aag gct ttc agc cca gaa gtg ata ccc atg ttt tca gca tta tca      96
```

-continued

```
gaa gga gcc acc cca caa gat tta aat acc atg cta aac aca gtg ggg       144
Glu Gly Ala Thr Pro Gln Asp Leu Asn Thr Met Leu Asn Thr Val Gly
        35                  40                  45 gga cat caa gca gcc atg caa atg tta aaa gag acc atc aat gag gaa       192
Gly His Gln Ala Ala Met Gln Met Leu Lys Glu Thr Ile Asn Glu Glu
    50                  55                  60 gct gca gaa tgg gat aga gtg cat cca gtg cat gca ggg cct att gca       240
Ala Ala Glu Trp Asp Arg Val His Pro Val His Ala Gly Pro Ile Ala
65                  70                  75                  80 cca ggc cag atg aga gaa cca agg gga agt gat ata gca gga act act       288
Pro Gly Gln Met Arg Glu Pro Arg Gly Ser Asp Ile Ala Gly Thr Thr
                85                  90                  95 agt acc ctt cag ctc gag gga tcc ggg ccc tct aga tgc ggc cgc atg       336
Ser Thr Leu Gln Leu Glu Gly Ser Gly Pro Ser Arg Cys Gly Arg Met
            100                 105                 110 cat ggt acc taa                                                       348
His Gly Thr
        115

<210> SEQ ID NO 19
<211> LENGTH: 115
<212> TYPE: PRT
<213> ORGANISM: Human immunodeficiency virus type 1

<400> SEQUENCE: 19

Met Thr Met Ile Thr Pro Ser Leu Ala Ala Trp Val Lys Val Ile Glu
1               5                   10                  15

Glu Lys Ala Phe Ser Pro Glu Val Ile Pro Met Phe Ser Ala Leu Ser
            20                  25                  30

Glu Gly Ala Thr Pro Gln Asp Leu Asn Thr Met Leu Asn Thr Val Gly
        35                  40                  45

Gly His Gln Ala Ala Met Gln Met Leu Lys Glu Thr Ile Asn Glu Glu
    50                  55                  60

Ala Ala Glu Trp Asp Arg Val His Pro Val His Ala Gly Pro Ile Ala
65                  70                  75                  80

Pro Gly Gln Met Arg Glu Pro Arg Gly Ser Asp Ile Ala Gly Thr Thr
                85                  90                  95

Ser Thr Leu Gln Leu Glu Gly Ser Gly Pro Ser Arg Cys Gly Arg Met
            100                 105                 110

His Gly Thr
        115

<210> SEQ ID NO 20
<211> LENGTH: 648
<212> TYPE: DNA
<213> ORGANISM: Human immunodeficiency virus type 1
<220> FEATURE:
<221> NAME/KEY: CDS
<222> LOCATION: (1)..(645)

<400> SEQUENCE: 20 atg acc atg att acg cca agc ttg gct gca tgg gta aaa gta ata gaa        48
Met Thr Met Ile Thr Pro Ser Leu Ala Ala Trp Val Lys Val Ile Glu
1               5                   10                  15 gaa aag gct ttc agc cca gaa gtg ata ccc atg ttt tca gca tta tca        96
Glu Lys Ala Phe Ser Pro Glu Val Ile Pro Met Phe Ser Ala Leu Ser
            20                  25                  30 gaa gga gcc acc cca caa gat tta aat acc atg cta aac aca gtg ggg       144
```

```
Glu Gly Ala Thr Pro Gln Asp Leu Asn Thr Met Leu Asn Thr Val Gly
            35                  40                  45 gga cat caa gca gcc atg caa atg tta aaa gag acc atc aat gag gaa     192
Gly His Gln Ala Ala Met Gln Met Leu Lys Glu Thr Ile Asn Glu Glu
 50                  55                  60 gct gca gaa tgg gat aga gtg cat cca gtg cat gca ggg cct att gca     240
Ala Ala Glu Trp Asp Arg Val His Pro Val His Ala Gly Pro Ile Ala
 65                  70                  75                  80 cca ggc cag atg aga gaa cca agg gga agt gat ata gca gga act act     288
Pro Gly Gln Met Arg Glu Pro Arg Gly Ser Asp Ile Ala Gly Thr Thr
                 85                  90                  95 agt acc ctt cag gaa caa ata gga tgg atg aca aac aat cca cct atc     336
Ser Thr Leu Gln Glu Gln Ile Gly Trp Met Thr Asn Asn Pro Pro Ile
            100                 105                 110 cca gta gga gaa atc tat aaa aga tgg ata atc ctg gga tta aat aaa     384
Pro Val Gly Glu Ile Tyr Lys Arg Trp Ile Ile Leu Gly Leu Asn Lys
        115                 120                 125 ata gta aga atg tat agt cct gtt agt att ctg gac ata aga caa gga     432
Ile Val Arg Met Tyr Ser Pro Val Ser Ile Leu Asp Ile Arg Gln Gly
    130                 135                 140 cca aag gaa ccc ttt aga gac tat gta gat cgg ttc tat aaa act tta     480
Pro Lys Glu Pro Phe Arg Asp Tyr Val Asp Arg Phe Tyr Lys Thr Leu
145                 150                 155                 160 aga gcc gag caa gct tca cag gag gta aaa aat tgg atg aca gaa acc     528
Arg Ala Glu Gln Ala Ser Gln Glu Val Lys Asn Trp Met Thr Glu Thr
                165                 170                 175 ttg ttg gtc caa aat gcg aac cca gac tgt aag act att cta aaa gca     576
Leu Leu Val Gln Asn Ala Asn Pro Asp Cys Lys Thr Ile Leu Lys Ala
            180                 185                 190 tta gga cca gca gct aca cta gaa ctc gag gga tcc ggg ccc tct aga     624
Leu Gly Pro Ala Ala Thr Leu Glu Leu Glu Gly Ser Gly Pro Ser Arg
        195                 200                 205 tgc ggc cgc atg cat ggt acc taa                                     648
Cys Gly Arg Met His Gly Thr
    210                 215

<210> SEQ ID NO 21
<211> LENGTH: 215
<212> TYPE: PRT
<213> ORGANISM: Human immunodeficiency virus type 1

<400> SEQUENCE: 21

Met Thr Met Ile Thr Pro Ser Leu Ala Ala Trp Val Lys Val Ile Glu
 1               5                  10                  15

Glu Lys Ala Phe Ser Pro Glu Val Ile Pro Met Phe Ser Ala Leu Ser
            20                  25                  30

Glu Gly Ala Thr Pro Gln Asp Leu Asn Thr Met Leu Asn Thr Val Gly
        35                  40                  45

Gly His Gln Ala Ala Met Gln Met Leu Lys Glu Thr Ile Asn Glu Glu
 50                  55                  60

Ala Ala Glu Trp Asp Arg Val His Pro Val His Ala Gly Pro Ile Ala
 65                  70                  75                  80

Pro Gly Gln Met Arg Glu Pro Arg Gly Ser Asp Ile Ala Gly Thr Thr
                 85                  90                  95

Ser Thr Leu Gln Glu Gln Ile Gly Trp Met Thr Asn Asn Pro Pro Ile
            100                 105                 110

Pro Val Gly Glu Ile Tyr Lys Arg Trp Ile Ile Leu Gly Leu Asn Lys
        115                 120                 125
```

```
Ile Val Arg Met Tyr Ser Pro Val Ser Ile Leu Asp Ile Arg Gln Gly
    130                 135                 140

Pro Lys Glu Pro Phe Arg Asp Tyr Val Asp Arg Phe Tyr Lys Thr Leu
145                 150                 155                 160

Arg Ala Glu Gln Ala Ser Gln Glu Val Lys Asn Trp Met Thr Glu Thr
                165                 170                 175

Leu Leu Val Gln Asn Ala Asn Pro Asp Cys Lys Thr Ile Leu Lys Ala
            180                 185                 190

Leu Gly Pro Ala Ala Thr Leu Glu Leu Glu Gly Ser Gly Pro Ser Arg
        195                 200                 205

Cys Gly Arg Met His Gly Thr
    210                 215

<210> SEQ ID NO 22
<211> LENGTH: 363
<212> TYPE: DNA
<213> ORGANISM: Human immunodeficiency virus type 1
<220> FEATURE:
<221> NAME/KEY: CDS
<222> LOCATION: (1)..(360)

<400> SEQUENCE: 22 atg gct agc gaa ttc gaa caa ata gga tgg atg aca aac aat cca cct     48
Met Ala Ser Glu Phe Glu Gln Ile Gly Trp Met Thr Asn Asn Pro Pro
1               5                   10                  15 atc cca gta gga gaa atc tat aaa aga tgg ata atc ctg gga tta aat     96
Ile Pro Val Gly Glu Ile Tyr Lys Arg Trp Ile Ile Leu Gly Leu Asn
                20                  25                  30 aaa ata gta aga atg tat agt cct gtt agt att ctg gac ata aga caa    144
Lys Ile Val Arg Met Tyr Ser Pro Val Ser Ile Leu Asp Ile Arg Gln
            35                  40                  45 gga cca aag gaa ccc ttt aga gac tat gta gtt cgg ttc tat aaa act    192
Gly Pro Lys Glu Pro Phe Arg Asp Tyr Val Val Arg Phe Tyr Lys Thr
        50                  55                  60 tta aga gcc gag caa gct tca cag gag gta aaa aat tgg atg aca gaa    240
Leu Arg Ala Glu Gln Ala Ser Gln Glu Val Lys Asn Trp Met Thr Glu
65                  70                  75                  80 acc ttg ttg gtc caa aat gcg aac cca gac tgt aag act att cta aaa    288
Thr Leu Leu Val Gln Asn Ala Asn Pro Asp Cys Lys Thr Ile Leu Lys
                85                  90                  95 gca tta gga cca gca gct aca cta gaa ctc gag gga tcc ggg ccc tct    336
Ala Leu Gly Pro Ala Ala Thr Leu Glu Leu Glu Gly Ser Gly Pro Ser
            100                 105                 110 aga tgc ggc cgc atg cat ggt acc taa                                363
Arg Cys Gly Arg Met His Gly Thr
        115                 120

<210> SEQ ID NO 23
<211> LENGTH: 120
<212> TYPE: PRT
<213> ORGANISM: Human immunodeficiency virus type 1

<400> SEQUENCE: 23

Met Ala Ser Glu Phe Glu Gln Ile Gly Trp Met Thr Asn Asn Pro Pro
1               5                   10                  15

Ile Pro Val Gly Glu Ile Tyr Lys Arg Trp Ile Ile Leu Gly Leu Asn
                20                  25                  30

Lys Ile Val Arg Met Tyr Ser Pro Val Ser Ile Leu Asp Ile Arg Gln
            35                  40                  45

Gly Pro Lys Glu Pro Phe Arg Asp Tyr Val Val Arg Phe Tyr Lys Thr
```

```
                        50                      55                      60
Leu Arg Ala Glu Gln Ala Ser Gln Glu Val Lys Asn Trp Met Thr Glu
 65                      70                      75                      80

Thr Leu Leu Val Gln Asn Ala Asn Pro Asp Cys Lys Thr Ile Leu Lys
                 85                      90                      95

Ala Leu Gly Pro Ala Ala Thr Leu Glu Leu Glu Gly Ser Gly Pro Ser
                100                     105                     110

Arg Cys Gly Arg Met His Gly Thr
            115                 120

<210> SEQ ID NO 24
<211> LENGTH: 594
<212> TYPE: DNA
<213> ORGANISM: Human immunodeficiency virus type 1
<220> FEATURE:
<221> NAME/KEY: CDS
<222> LOCATION: (1)..(591)

<400> SEQUENCE: 24 atg gct agc gaa ttc gaa caa ata gga tgg atg aca aac aat cca cct      48
Met Ala Ser Glu Phe Glu Gln Ile Gly Trp Met Thr Asn Asn Pro Pro
 1               5                  10                  15 atc cca gta gga gaa atc tat aaa aga tgg ata atc ctg gga tta aat      96
Ile Pro Val Gly Glu Ile Tyr Lys Arg Trp Ile Ile Leu Gly Leu Asn
                20                  25                  30 aaa ata gta aga atg tat agt cct gtt agt att ctg gac ata aga caa     144
Lys Ile Val Arg Met Tyr Ser Pro Val Ser Ile Leu Asp Ile Arg Gln
             35                  40                  45 gga cca aag gaa ccc ttt aga gac tat gta gat cgg ttc tat aaa act     192
Gly Pro Lys Glu Pro Phe Arg Asp Tyr Val Asp Arg Phe Tyr Lys Thr
         50                  55                  60 tta aga gcc gag caa gct tca cag gag gta aaa aat tgg atg aca gaa     240
Leu Arg Ala Glu Gln Ala Ser Gln Glu Val Lys Asn Trp Met Thr Glu
 65                  70                  75                  80 acc ttg ttg gtc caa aat gcg aac cca gac tgt aag act att cta aaa     288
Thr Leu Leu Val Gln Asn Ala Asn Pro Asp Cys Lys Thr Ile Leu Lys
                 85                  90                  95 gca tta gga cca gca gct aca cta gaa gaa atg atg aca gca tgt cag     336
Ala Leu Gly Pro Ala Ala Thr Leu Glu Glu Met Met Thr Ala Cys Gln
                100                 105                 110 gga gtg ggg gga ccc ggc cat aag gca aga gtg ttg gct gaa gca atg     384
Gly Val Gly Gly Pro Gly His Lys Ala Arg Val Leu Ala Glu Ala Met
            115                 120                 125 agc caa gta aca aat tca gct acc ata atg atg cag aga ggt aat ttt     432
Ser Gln Val Thr Asn Ser Ala Thr Ile Met Met Gln Arg Gly Asn Phe
        130                 135                 140 agg aac caa aaa aag act gtt aag tgt ttc aat tgt ggc aaa gaa ggg     480
Arg Asn Gln Lys Lys Thr Val Lys Cys Phe Asn Cys Gly Lys Glu Gly
145                 150                 155                 160 cac ata gcc aaa aat tgc agg gcc cct agg aaa aag ggc tgt tgg aaa     528
His Ile Ala Lys Asn Cys Arg Ala Pro Arg Lys Lys Gly Cys Trp Lys
                165                 170                 175 tgt gga aag gaa gga cac caa atg aaa gat tgt act gag aga cag gct     576
Cys Gly Lys Glu Gly His Gln Met Lys Asp Cys Thr Glu Arg Gln Ala
                180                 185                 190 aat ttt tta ggg aac taa                                             594
Asn Phe Leu Gly Asn
            195

<210> SEQ ID NO 25
```

```
<211> LENGTH: 197
<212> TYPE: PRT
<213> ORGANISM: Human immunodeficiency virus type 1

<400> SEQUENCE: 25

Met Ala Ser Glu Phe Glu Gln Ile Gly Trp Met Thr Asn Asn Pro Pro
1               5                   10                  15

Ile Pro Val Gly Glu Ile Tyr Lys Arg Trp Ile Ile Leu Gly Leu Asn
            20                  25                  30

Lys Ile Val Arg Met Tyr Ser Pro Val Ser Ile Leu Asp Ile Arg Gln
        35                  40                  45

Gly Pro Lys Glu Pro Phe Arg Asp Tyr Val Asp Arg Phe Tyr Lys Thr
    50                  55                  60

Leu Arg Ala Glu Gln Ala Ser Gln Glu Val Lys Asn Trp Met Thr Glu
65                  70                  75                  80

Thr Leu Leu Val Gln Asn Ala Asn Pro Asp Cys Lys Thr Ile Leu Lys
                85                  90                  95

Ala Leu Gly Pro Ala Ala Thr Leu Glu Glu Met Met Thr Ala Cys Gln
            100                 105                 110

Gly Val Gly Gly Pro Gly His Lys Ala Arg Val Leu Ala Glu Ala Met
        115                 120                 125

Ser Gln Val Thr Asn Ser Ala Thr Ile Met Met Gln Arg Gly Asn Phe
    130                 135                 140

Arg Asn Gln Lys Lys Thr Val Lys Cys Phe Asn Cys Gly Lys Glu Gly
145                 150                 155                 160

His Ile Ala Lys Asn Cys Arg Ala Pro Arg Lys Lys Gly Cys Trp Lys
                165                 170                 175

Cys Gly Lys Glu Gly His Gln Met Lys Asp Cys Thr Glu Arg Gln Ala
            180                 185                 190

Asn Phe Leu Gly Asn
        195

<210> SEQ ID NO 26
<211> LENGTH: 294
<212> TYPE: DNA
<213> ORGANISM: Human immunodeficiency virus type 1
<220> FEATURE:
<221> NAME/KEY: CDS
<222> LOCATION: (1)..(291)

<400> SEQUENCE: 26 atg gct agc gaa ttc gaa atg atg aca gca tgt cag gga gtg ggg gga      48
Met Ala Ser Glu Phe Glu Met Met Thr Ala Cys Gln Gly Val Gly Gly
1               5                   10                  15 ccc ggc cat aag gca aga gtg ttg gct gaa gca atg agc caa gta aca      96
Pro Gly His Lys Ala Arg Val Leu Ala Glu Ala Met Ser Gln Val Thr
            20                  25                  30 aat tca gct acc ata atg atg cag aga ggt aat ttt agg aac caa aaa     144
Asn Ser Ala Thr Ile Met Met Gln Arg Gly Asn Phe Arg Asn Gln Lys
        35                  40                  45 aaa act gtt aag tgt ttc aat tgt ggc aaa gaa ggg cac ata gcc aaa     192
Lys Thr Val Lys Cys Phe Asn Cys Gly Lys Glu Gly His Ile Ala Lys
    50                  55                  60 aat tgc agg gcc cct agg aaa aag ggc tgt tgg aaa tgt gga aag gaa     240
Asn Cys Arg Ala Pro Arg Lys Lys Gly Cys Trp Lys Cys Gly Lys Glu
65                  70                  75                  80 gga cac caa atg aaa gat tgt act gag aga cag gct aat ttt tta ggg     288
Gly His Gln Met Lys Asp Cys Thr Glu Arg Gln Ala Asn Phe Leu Gly
                85                  90                  95
```

```
aac taa                                                          294
Asn

<210> SEQ ID NO 27
<211> LENGTH: 97
<212> TYPE: PRT
<213> ORGANISM: Human immunodeficiency virus type 1

<400> SEQUENCE: 27

Met Ala Ser Glu Phe Glu Met Met Thr Ala Cys Gln Gly Val Gly Gly
1               5                   10                  15

Pro Gly His Lys Ala Arg Val Leu Ala Glu Ala Met Ser Gln Val Thr
            20                  25                  30

Asn Ser Ala Thr Ile Met Met Gln Arg Gly Asn Phe Arg Asn Gln Lys
        35                  40                  45

Lys Thr Val Lys Cys Phe Asn Cys Gly Lys Glu Gly His Ile Ala Lys
    50                  55                  60

Asn Cys Arg Ala Pro Arg Lys Lys Gly Cys Trp Lys Cys Gly Lys Glu
65                  70                  75                  80

Gly His Gln Met Lys Asp Cys Thr Glu Arg Gln Ala Asn Phe Leu Gly
                85                  90                  95

Asn

<210> SEQ ID NO 28
<211> LENGTH: 399
<212> TYPE: DNA
<213> ORGANISM: Human immunodeficiency virus type 1
<220> FEATURE:
<221> NAME/KEY: CDS
<222> LOCATION: (1)..(396)

<400> SEQUENCE: 28 atg gct agc gaa ttc cct ata gtg cag aac atc cag ggg caa atg gta    48
Met Ala Ser Glu Phe Pro Ile Val Gln Asn Ile Gln Gly Gln Met Val
1               5                   10                  15 cat cag gcc ata tca cct aga act tta aat gca tgg gta aaa gta ata    96
His Gln Ala Ile Ser Pro Arg Thr Leu Asn Ala Trp Val Lys Val Ile
            20                  25                  30 gaa gaa aag gct ttc agc cca gaa gtg ata ccc atg ttt tca gca tta   144
Glu Glu Lys Ala Phe Ser Pro Glu Val Ile Pro Met Phe Ser Ala Leu
        35                  40                  45 tca gaa gga gcc acc cca caa gat tta aat acc atg cta aac aca gtg   192
Ser Glu Gly Ala Thr Pro Gln Asp Leu Asn Thr Met Leu Asn Thr Val
    50                  55                  60 ggg gga cat caa gca gcc atg caa atg tta aaa gag acc atc aat gag   240
Gly Gly His Gln Ala Ala Met Gln Met Leu Lys Glu Thr Ile Asn Glu
65                  70                  75                  80 gaa gct gca gaa tgg gat aga gtg cat cca gtg cat gca ggg cct att   288
Glu Ala Ala Glu Trp Asp Arg Val His Pro Val His Ala Gly Pro Ile
                85                  90                  95 gca cca ggc cag atg aga gaa cca agg gga agt gat ata gca gga act   336
Ala Pro Gly Gln Met Arg Glu Pro Arg Gly Ser Asp Ile Ala Gly Thr
                100                 105                 110 act agt acc ctt cag ctc gag gga tcc ggg ccc tct aga tgc ggc cgc   384
Thr Ser Thr Leu Gln Leu Glu Gly Ser Gly Pro Ser Arg Cys Gly Arg
            115                 120                 125 atg cat ggt acc taa                                               399
Met His Gly Thr
    130
```

-continued

```
<210> SEQ ID NO 29
<211> LENGTH: 132
<212> TYPE: PRT
<213> ORGANISM: Human immunodeficiency virus type 1

<400> SEQUENCE: 29

Met Ala Ser Glu Phe Pro Ile Val Gln Asn Ile Gln Gly Gln Met Val
1               5                   10                  15

His Gln Ala Ile Ser Pro Arg Thr Leu Asn Ala Trp Val Lys Val Ile
            20                  25                  30

Glu Glu Lys Ala Phe Ser Pro Glu Val Ile Pro Met Phe Ser Ala Leu
        35                  40                  45

Ser Glu Gly Ala Thr Pro Gln Asp Leu Asn Thr Met Leu Asn Thr Val
    50                  55                  60

Gly Gly His Gln Ala Ala Met Gln Met Leu Lys Glu Thr Ile Asn Glu
65                  70                  75                  80

Glu Ala Ala Glu Trp Asp Arg Val His Pro Val His Ala Gly Pro Ile
                85                  90                  95

Ala Pro Gly Gln Met Arg Glu Pro Arg Gly Ser Asp Ile Ala Gly Thr
            100                 105                 110

Thr Ser Thr Leu Gln Leu Glu Gly Ser Gly Pro Ser Arg Cys Gly Arg
        115                 120                 125

Met His Gly Thr
    130

<210> SEQ ID NO 30
<211> LENGTH: 231
<212> TYPE: PRT
<213> ORGANISM: Human immunodeficiency virus type 1

<400> SEQUENCE: 30

Met Pro Val Gln Gln Thr Gly Gly Gly Asn Tyr Ile His Val Pro Leu
1               5                   10                  15

Ser Pro Arg Thr Leu Asn Ala Trp Val Lys Leu Val Glu Asp Lys Lys
            20                  25                  30

Phe Gly Ala Glu Val Val Pro Gly Phe Gln Ala Leu Ser Glu Gly Cys
        35                  40                  45

Thr Pro Tyr Asp Ile Asn Gln Met Leu Asn Cys Val Gly Asp His Gln
    50                  55                  60

Ala Ala Met Gln Ile Ile Arg Glu Ile Ile Asn Asp Glu Ala Ala Asp
65                  70                  75                  80

Trp Asp Ala Gln His Pro Ile Pro Gly Pro Leu Pro Ala Gly Gln Leu
                85                  90                  95

Arg Asp Pro Arg Gly Ser Asp Ile Ala Gly Thr Thr Ser Thr Val Glu
            100                 105                 110

Glu Gln Ile Gln Trp Met Tyr Arg Pro Gln Asn Pro Val Pro Val Gly
        115                 120                 125

Asn Ile Tyr Arg Arg Trp Ile Gln Ile Gly Leu Gln Lys Cys Val Arg
    130                 135                 140

Met Tyr Asn Pro Thr Asn Ile Leu Asp Val Lys Gln Gly Pro Lys Glu
145                 150                 155                 160

Pro Phe Gln Ser Tyr Val Asp Arg Phe Tyr Lys Ser Leu Arg Ala Glu
                165                 170                 175

Gln Thr Asp Pro Ala Val Lys Asn Trp Met Thr Gln Thr Leu Leu Ile
            180                 185                 190
```

```
Gln Asn Ala Asn Pro Asp Cys Lys Leu Val Leu Lys Gly Leu Gly Met
        195                 200                 205

Asn Pro Thr Leu Glu Glu Met Leu Thr Ala Cys Gln Gly Val Gly Gly
    210                 215                 220

Pro Gly Gln Lys Ala Arg Leu
225                 230

<210> SEQ ID NO 31
<211> LENGTH: 696
<212> TYPE: DNA
<213> ORGANISM: Human immunodeficiency virus type 1
<220> FEATURE:
<221> NAME/KEY: CDS
<222> LOCATION: (1)..(693)

<400> SEQUENCE: 31 atg cct gta caa cag aca ggc ggt ggc aac tat atc cac gtg cca ctg     48
Met Pro Val Gln Gln Thr Gly Gly Gly Asn Tyr Ile His Val Pro Leu
1               5                   10                  15 agc ccc cga act cta aat gct tgg gta aaa tta gta gag gac aag aag     96
Ser Pro Arg Thr Leu Asn Ala Trp Val Lys Leu Val Glu Asp Lys Lys
            20                  25                  30 ttc ggg gca gaa gta gtg cca gga ttt caa gca ctc tca gaa ggc tgc    144
Phe Gly Ala Glu Val Val Pro Gly Phe Gln Ala Leu Ser Glu Gly Cys
        35                  40                  45 acg ccc tat gat atc aac caa atg ctt aat tgt gtg ggc gat cac caa    192
Thr Pro Tyr Asp Ile Asn Gln Met Leu Asn Cys Val Gly Asp His Gln
    50                  55                  60 gca gct atg caa ata atc aga gag att atc aat gac gaa gca gca gat    240
Ala Ala Met Gln Ile Ile Arg Glu Ile Ile Asn Asp Glu Ala Ala Asp
65                  70                  75                  80 tgg gat gca cag cac cca ata cca ggc ccc tta cca gca ggg cag ctt    288
Trp Asp Ala Gln His Pro Ile Pro Gly Pro Leu Pro Ala Gly Gln Leu
                85                  90                  95 aga gac cca agg ggg tct gac ata gca gga aca aca agc aca gta gaa    336
Arg Asp Pro Arg Gly Ser Asp Ile Ala Gly Thr Thr Ser Thr Val Glu
            100                 105                 110 gaa cag atc cag tgg atg tat agg cca caa aat ccc gtg ccg gta ggg    384
Glu Gln Ile Gln Trp Met Tyr Arg Pro Gln Asn Pro Val Pro Val Gly
        115                 120                 125 aac atc tac aga aga tgg atc cag ata ggg cta cag aag tgt gtc agg    432
Asn Ile Tyr Arg Arg Trp Ile Gln Ile Gly Leu Gln Lys Cys Val Arg
    130                 135                 140 atg tac aac cca act aac atc tta gac gta aag cag gga cca aag gaa    480
Met Tyr Asn Pro Thr Asn Ile Leu Asp Val Lys Gln Gly Pro Lys Glu
145                 150                 155                 160 ccg ttc cag agc tat gtg gac agg ttc tat aaa agc ttg agg gca gaa    528
Pro Phe Gln Ser Tyr Val Asp Arg Phe Tyr Lys Ser Leu Arg Ala Glu
                165                 170                 175 caa aca gat ccg gca gta aag aac tgg atg acc caa acg ctg cta ata    576
Gln Thr Asp Pro Ala Val Lys Asn Trp Met Thr Gln Thr Leu Leu Ile
            180                 185                 190 cag aat gcc aac cca gac tgc aag tta gta cta aaa gga ctg ggg atg    624
Gln Asn Ala Asn Pro Asp Cys Lys Leu Val Leu Lys Gly Leu Gly Met
        195                 200                 205 aat ccc acc cta gaa gag atg ctg act gcc tgt cag ggg gta ggt gga    672
Asn Pro Thr Leu Glu Glu Met Leu Thr Ala Cys Gln Gly Val Gly Gly
    210                 215                 220 cca ggc caa aaa gcc aga cta taa                                    696
Pro Gly Gln Lys Ala Arg Leu
225                 230
```

```
<210> SEQ ID NO 32
<211> LENGTH: 231
<212> TYPE: PRT
<213> ORGANISM: Human immunodeficiency virus type 1

<400> SEQUENCE: 32

Met Pro Val Gln Gln Thr Gly Gly Asn Tyr Ile His Val Pro Leu
1               5                   10                  15

Ser Pro Arg Thr Leu Asn Ala Trp Val Lys Leu Val Glu Asp Lys Lys
            20                  25                  30

Phe Gly Ala Glu Val Val Pro Gly Phe Gln Ala Leu Ser Glu Gly Cys
            35                  40                  45

Thr Pro Tyr Asp Ile Asn Gln Met Leu Asn Cys Val Gly Asp His Gln
    50                  55                  60

Ala Ala Met Gln Ile Ile Arg Glu Ile Ile Asn Asp Glu Ala Ala Asp
65                  70                  75                  80

Trp Asp Ala Gln His Pro Ile Pro Gly Pro Leu Pro Ala Gly Gln Leu
                85                  90                  95

Arg Asp Pro Arg Gly Ser Asp Ile Ala Gly Thr Thr Ser Thr Val Glu
            100                 105                 110

Glu Gln Ile Gln Trp Met Tyr Arg Pro Gln Asn Pro Val Pro Val Gly
            115                 120                 125

Asn Ile Tyr Arg Arg Trp Ile Gln Ile Gly Leu Gln Lys Cys Val Arg
    130                 135                 140

Met Tyr Asn Pro Thr Asn Ile Leu Asp Val Lys Gln Gly Pro Lys Glu
145                 150                 155                 160

Pro Phe Gln Ser Tyr Val Asp Arg Phe Tyr Lys Ser Leu Arg Ala Glu
                165                 170                 175

Gln Thr Asp Pro Ala Val Lys Asn Trp Met Thr Gln Thr Leu Leu Ile
            180                 185                 190

Gln Asn Ala Asn Pro Asp Cys Lys Leu Val Leu Lys Gly Leu Gly Met
        195                 200                 205

Asn Pro Thr Leu Glu Glu Met Leu Thr Ala Cys Gln Gly Val Gly Gly
    210                 215                 220

Pro Gly Gln Lys Ala Arg Leu
225                 230
```